US007846900B2

(12) United States Patent
Vesely

(10) Patent No.: US 7,846,900 B2
(45) Date of Patent: *Dec. 7, 2010

(54) CANCER TREATMENT USING C-TYPE NATRIURETIC PEPTIDE

(75) Inventor: David L. Vesely, Tampa, FL (US)

(73) Assignee: University of South Florida, Tampa, FL (US)

(\*) Notice: Subject to any disclaimer, the term of this patent is extended or adjusted under 35 U.S.C. 154(b) by 0 days.

This patent is subject to a terminal disclaimer.

(21) Appl. No.: 12/346,192

(22) Filed: Dec. 30, 2008

(65) Prior Publication Data

US 2009/0170196 A1   Jul. 2, 2009

Related U.S. Application Data

(63) Continuation-in-part of application No. 10/908,604, filed on May 18, 2005, now Pat. No. 7,488,713, which is a continuation-in-part of application No. 10/708,688, filed on Mar. 18, 2004, now Pat. No. 6,943,147.

(60) Provisional application No. 60/320,018, filed on Mar. 19, 2003.

(51) Int. Cl.
A61K 38/00 (2006.01)
C07K 5/00 (2006.01)
C07K 7/00 (2006.01)

(52) U.S. Cl. ............................ 514/12; 514/13; 530/324; 530/326

(58) Field of Classification Search ................ None
See application file for complete search history.

(56) References Cited

U.S. PATENT DOCUMENTS

| 4,753,945 A | 6/1988 | Gilbard et al. |
| 5,545,614 A | 8/1996 | Stamler et al. |
| 5,602,143 A | 2/1997 | Krauss |
| 5,625,056 A | 4/1997 | Genieser et al. |
| 5,665,861 A | 9/1997 | Forssmann et al. |
| 5,858,694 A | 1/1999 | Piazza et al. |
| 2002/0094326 A1 | 7/2002 | Donahue et al. |
| 2003/0105000 A1 | 6/2003 | Pero et al. |
| 2004/0229784 A1 | 11/2004 | Vesely |
| 2005/0176641 A1 | 8/2005 | Bakis et al. |
| 2005/0209139 A1 | 9/2005 | Vesely |
| 2005/0272650 A1 | 12/2005 | Mohapatra |
| 2006/0014689 A1 | 1/2006 | Vesely |
| 2006/0019256 A1 | 1/2006 | Clarke et al. |
| 2006/0276382 A1 | 12/2006 | Mohapatra |
| 2007/0265204 A1 | 11/2007 | Mohapatra et al. |
| 2008/0039394 A1 | 2/2008 | Vesely |
| 2008/0070858 A1 | 3/2008 | Mohapatra |
| 2008/0214437 A1 | 9/2008 | Mohapatra et al. |
| 2009/0062206 A1 | 3/2009 | Vesely |
| 2009/0176706 A1 | 7/2009 | Mohapatra |

FOREIGN PATENT DOCUMENTS

| WO | WO 2004/022003 A3 | 3/2004 |
| WO | WO 2004/083236 A3 | 9/2004 |
| WO | WO 2005/094420 A3 | 10/2005 |
| WO | WO 2006/026536 A3 | 3/2006 |
| WO | WO 2007/127487 A3 | 11/2007 |
| WO | WO 2007/130672 A3 | 11/2007 |
| WO | WO 2009/073527 A3 | 6/2009 |

OTHER PUBLICATIONS

ATCC No. CCL-248 (T84, 1984).
Benjamin, B.A. et al. "Effect of proANF-(31-67) on sodium excretion in conscious monkeys" *Am J Physiol Regul Integr Comp Physiol*, 1995, pp. R1351-R1355, vol. 269, abstract.
Buskens, C. et al. "Adenocarcinomas of the Gastro-Esophageal Junction: A Comparative Study of the Gastric Cardia and the Esophagus with Respect to Cyclooxygenase-2 Expression" *Digestive Disease Week Abstracts and Itinerary Planner*, 2003, Abstract No. 850.
Capizzi, R.L. "Molecular and Cellular Biology of Cancer" In: Internal Medicine, 4th Edition, Ed. Jay Stein, Elsevier Science, 1994, pp. 707-729.
Carter, S.K. et al. "Chemotheraphy of Cancer" Second Edition, John Wiley & Sons: New York, 1981, Appendix C.
Chow, W.H. et al. "Rising Incidence of Renal Cell Cancer in the United States" *JAMA*, May 1999, pp. 1628-1631, vol. 281, No. 17.

(Continued)

*Primary Examiner*—Maryam Monshipouri
*Assistant Examiner*—Marsha M Tsay
(74) *Attorney, Agent, or Firm*—Saliwanchik, Lloyd & Saliwanchik

(57) ABSTRACT

The present invention includes a method of utilizing four peptide hormones to inhibit the growth of cancer(s). A dramatic decrease in the number of human pancreatic adenocarcinoma cells (i.e., the type of cancer with the highest mortality, with patients only surviving four months) was observed responsive to treatment. The application of the invention would be to utilize one or more of these peptide hormones alone and/or in combination to treat cancer. The ability of these peptide hormones to decrease the number of adenocarcinoma cells has implications for adenocarcinomas at other sites in the body with the majority of cancers of the breast, colon and prostate also being adenocarcinomas. Adenocarcinomas also occur in the lung and other tissues. Treatment of a wide variety of cancers in addition to adenocarcinomas is anticipated by the present invention.

6 Claims, 15 Drawing Sheets

OTHER PUBLICATIONS

Clark, J.I. et al. "Adjuvant High-Dose Bolus Interleukin-2 for Patients With High-Risk Renal Cell Carcinoma: A Cytokine Working Group Randomized Trial" *Journal of Clinical Oncology*, Aug. 15, 2003, pp. 3133-3140, vol. 21, No. 16.

Cohen, H.T. et al. "Medical Progress: Renal-Cell Carcinoma" *The New England Journal of Medicine*, Dec. 8, 2005, pp. 2477-2490, vol. 353, No. 23.

Daggubati, S. et al. "Adrenomedullin, endothelin, neuropeptide Y, atrial, brain, and C-natriuretic prohormone peptides compared as early heart failure indicators" *Cardiovascular Research*, 1997, pp. 246-255, vol. 36.

De Palo, E.F. et al. "Circulating Immunoreactive proANP(1-30) and proANP(31-67) in Sedentary Subjects and Athletes" *Clinical Chemistry*, 2000, pp. 843-847, vol. 46, No. 6.

Dermer, G.B. "The Last Word: Another Anniversary for the War on Cancer" *Bio/Technology*, Mar. 1994, p. 320, vol. 12.

Dietz, J.R. et al. "Evidence supporting a physiological role for proANP-(1-30) in the regulation of renal excretion" *Am J Physiol Regul Integr Comp Physiol*, 2001, pp. R1510-R1517, vol. 280.

Fisher, E. et al. "Comparative Histopathologic, Histochemical, Electron Microscopic and Tissue Culture Studies of Bronchial Carcinoids and Oat Cell Carcinomas of Lung" *Am J Clin Pathol*, 1978, pp. 165-172, vol. 69.

Franz, M. et al. "N-terminal fragments of the proatrial natriuretic peptide in patients before and after hemodialysis treatment" *Kidney International*, 2000, pp. 374-383, vol. 58.

Franz, M. et al. "Plasma concentration and urinary excretion of N-terminal proatrial natriuretic peptides in patients with kidney diseases" *Kidney International*, 2001, pp. 1928-1934, vol. 59.

Freshney, R.I. "Culture of Animal Cells: A Manual of Basic Technique" Alan R. Liss, Inc.: New York, 1983, pp. 3-4.

Friedman, H.S. et al. "Glioblastoma Multiforme and the Epidermal Growth Factor Receptor" *N Engl J Med*, Nov. 2005, pp. 1997-1999, vol. 353, No. 19.

Garrett, M.D. et al. "Discovering Novel Chemotherapeutic Drugs for the Third Millennium" *European Journal of Cancer*, 1999, pp. 2010-2030, vol. 35, No. 14.

Gower, W.R. et al. "Four Peptides Decrease Human Colon Adenocarcinoma Cell Number and DNA Synthesis via Cyclic GMP" *International Journal of Gastrointestinal Cancer*, 2005, pp. 77-88, vol. 36, No. 2.

Gratzner, H.G., "Monoclonal Antibody to 5-Bromo- and 5-Iododeoxyuridine: A New Reagent for Detection of DNA Replication" *Science*, Oct. 29, 1982, pp. 474-475, vol. 218.

Gunning, M.E. et al. "Atrial Natriuretic Peptide$_{(31-67)}$ Inhibits Na$^+$ Transport in Rabbit Inner Medullary Collecting Duct Cells: Role of Prostaglandin E$_2$" *Journal of Clinical Investigation*, May 1992, pp. 1411-1417, vol. 89.

Gura, T. "Cancer Models: Systems for Identifying New Drugs are Often Faulty" *Science*, Nov. 7, 1997, pp. 1041-1042, vol. 278.

Heim, J.M. et al. "Urodilatin and β-ANF: Binding Properties and Activation of Particulate Guanylate Cyclase" *Biochemical and Biophysical Research Communications*, Aug. 30, 1989, pp. 37-41, vol. 163, No. 1.

Hunter, E.F.M. et al. "Analysis of peptides derived from Pro Atrial Natriuretic Peptide that circulate in man and increase in heart disease" *Scandinavian Journal of Clinical and Laboratory Investigation*, 1998, pp. 205-216, vol. 58.

Jemal, A. et al. "Cancer Statistics, 2005" *CA: A Cancer Journal for Clinicians*, 2005, pp. 10-30, vol. 55.

Kaiser, J. et al. "Cancer: First Pass at Cancer Genome Reveals Complex Landscape" *Science*, Sep. 8, 2006, p. 1370, vol. 313.

Krontiris, T.G. "Molecular and Cellular Biology of Cancer" In: Internal Medicine, 4th Edition, Ed. Jay Stein, Elsevier Science, 1994, pp. 699-707.

Kumar, R. et al. "Stimulation of atrial natriuretic peptide receptor/guanylyl cyclase- A signaling pathway antagonizes the activation of protein kinase C-α in murine Leydig cells" *Biochimica et Biophysica Acta*, 1997, pp. 221-228, vol. 1356.

La Vecchia, C. et al. "Smoking and Renal Cell Carcinoma" *Cancer Research*, Sep. 1, 1990, pp. 5231-5233, vol. 50.

Linder, M.W. et al. "Pharmacogenetics: a laboratory tool for optimizing therapeutic efficiency" *Clinical Chemistry*, 1997, pp. 254-266, vol. 43, No. 2.

Martin, D.R. et al. "Three peptides from the ANF prohormone NH$_2$ are natriuretic and/or kaliuretic" *Am J Physio Renal Physiol*, Dec. 1990, pp. F1401-F1408, vol. 258, abstract.

McLaughlin, J.K. et al. "A Population-Based Case-Control Study of Renal Cell Carcinoma", *J Natl Cancer Inst*, Feb. 1984, pp. 275-284, vol. 72.

Mellinghoff, I.K. et al. "Molecular Determinants of the Response of Glioblastomas to EGFR Kinase Inhibitors" *The New England Journal of Medicine*, Nov. 2005, pp. 2012-2024, vol. 353, No. 19.

Morstyn, G. et al. "Immunohistochemical Identification of Proliferating Cells in Organ Culture Using Bromodeoxyuridine and a Monoclonal Antiobody" *The Journal of Histochemistry and Cytochemistry*, 1986, pp. 697-701, vol. 34, No. 6.

Nguyen, T.D. et al. "Citrus Flavonoids Stimulate Secretion by Human Colonic $T_{84}$ Cells" *The Journal of Nutrition*, 1993, pp. 259-268, vol. 123.

Pan, E. et al. "Central Nervous System: Primary Neoplasms of the Central Nervous System" In: Kufe, D.W., Pollock, R.F., Weichselbaum, R.R., Bast, R.C., Jr., Gansler, I.S., Holland, J.F., and Frei, E., III (Eds.), Cancer Medicine, 6$^{th}$ Edition, 2003, pp. 1193-1226, London: BC Decker.

Pitari, G.M. et al. "Guanylyl cyclase C agonists regulate progression through the cell cycle of human colon carcinoma cells" *PNAS*, Jul. 3, 2001, pp. 7846-7851, vol. 98, No. 14.

Ropper, A.H. and Brown, R.H. (eds) "Intracranial Neoplasms and Paraneoplastic Disorders" In: Adams and Victor's Principles of Neurology, 8th Edition, 2005, New York: McGraw-Hill, pp. 546-591.

Rosenzweig, A. et al. "Atrial Natriuretic Factor and Related Peptide Hormones" *Annual Review of Biochemistry*, 1991, pp. 229-255, vol. 60.

Saba, S.R. et al. "Immunocytochemical Localization of Atrial Natriuretic Peptide, Vessel Dilator, Long-acting Natriuretic Peptide, and Kaliuretic Peptide in Human Pancreatic Adenocarcinomas" *Journal of Histochemistry & Cytochemistry*, 2005, pp. 989-995, vol. 53, No. 8.

Salani, D. et al. "Endothelin-1 Induces an Angiogenic Phenotype in Cultured Endothelial Cells and Stimulates Neovascularization In Vivo" *American Journal of Pathology*, Nov. 2000, pp. 1703-1711, vol. 157, No. 5.

Saxenhofer, H. et al. "Urodilatin: binding properties and stimulation of cGMP generation in rat kidney cells" *Am J Physiol Renal Physiol*, 1993, pp. F267-F273, vol. 264, abstract.

Schulz-Knappe, P. et al. "Isolation and Structural Analysis of "Urodilatin", a New Peptide of the Cardiodilatin-(ANP)-Family, Extracted from Human Urine" *Klinische Wochenschrift*, 1988, pp. 752-759, vol. 66.

Schwede, F. et al. "Cyclic nucleotide analogs as biochemical tools and prospective drugs" *Pharmacology & Therapeutics*, 2000, pp. 199-226, vol. 87.

Schweitz, H. et al. "A New Member of the Natriuretic Peptide Family Is Present in the Venom of the Green Mamba (*Dendroaspis angusticeps*)" *The Journal of Biological Chemistry*, Jul. 1992, pp. 13928-13932, vol. 267, No. 20.

Scott, D.A. et al. "The Pendred syndrome gene encodes a chloride-iodide transport protein" *Nature Genetics*, Apr. 1999, pp. 440-443, vol. 21.

Shapiro, J.A. et al. "Body Mass Index and Risk of Renal Cell Carcinoma" *Epidemiology*, Mar. 1999, pp. 188-191, vol. 10, No. 2.

Senger, D. et al. "Long-Term Survivors of Glioblastoma: Statistical Aberration or Important Unrecognized Molecular Subtype?" *The Cancer Journal*, May/Jun. 2003, pp. 214-221, vol. 9, No. 3.

Sudoh, T. et al. "C-Type Natriuretic Peptide (CNP): A New Member of Natriuretic Peptide Family Identified in Porcine Brain" *Biochemical and Biophysical Research Communications*, Apr. 30, 1990, pp. 863-870, vol. 168, No. 2.

Turner, G.A. et al. "Urine cyclic nucleotide concentrations in cancer and other conditions; cyclic GMP: a potential marker for cancer treatment" *J Clin Pathol*, 1982, pp. 800-806, vol. 35.

Valentin, J.P. et al. "Urodilatin Binds to and Activates Renal Receptors for Atrial Natriuretic Peptide" *Hypertension*, 1993, pp. 432-438, vol. 21.

Van Meir, E.G. et al. "Release of an inhibitor of angiogenesis upon induction of wild type *p53* expression in glioblastoma cells" *Nature Genetics*, Oct. 1994, pp. 171-176, vol. 8.

Vesely, B.A. et al. "Five cardiac hormones decrease the number of human small-cell lung cancer cells" *European Journal of Clinical Investigation*, 2005, pp. 388-398, vol. 35.

Vesely, B.A. et al. "Four cardiac hormones cause cell death in 81% of human ovarian adenocarcinoma cells" *Cancer Therapy*, 2007, pp. 97-104, vol. 5, Issue A.

Vesely, B.A. et al. "Four cardiac hormones eliminate 4-fold more human glioblastoma cells than the green mamba snake peptide" *Cancer Letters*, 2007, 254:94-101.

Vesely, B.A. et al. "Four peptide hormones decrease the number of human breast adenocarcinoma cells" *European Journal of Clinical Investigation*, 2005, pp. 60-69, vol. 35.

Vesely, B.A. et al. "Four peptide hormones' specific decrease (up to 97%) of human prostate carcinoma cells" *European Journal of Clinical Investigation*, 2005, pp. 700-710, vol. 35, No. 11.

Vesely, B.A. et al. "Four peptides decrease the number of human pancreatic adenocarcinoma cells" *European Journal of Clinical Investigation*, 2003, pp. 998-1005, vol. 33, No. 11.

Vesely, B.A. et al. "Primary Malignant Tumors of the Heart: Four Cardiovascular Hormones Decrease the Number and DNA Synthesis of Human Angiosarcoma Cells" *Cardiology*, 2006, pp. 226-233, vol. 105.

Vesely, B.A. et al. "Vessel dilator: Most potent of the atrial natriuretic peptides in decreasing the number and DNA synthesis of human squamous lung cancer cells" *Cancer Letters*, 2006, pp. 226-231, vol. 233.

Vesely, D.L. et al. "Atrial Natriuretic Peptide Increases Urodilatin in the Circulation", *American Journal of Nephrology*, 1998, pp. 204-213, vol. 18, abstract.

Vesely, D.L. et al. "Atrial natriuretic peptides in pathophysiological diseases" *Cardiovascular Research*, Sep. 2001, pp. 647-658, vol. 51, No. 4.

Vesely, D.L. et al. "Atrial Natriuretic Prohormone Peptides 1-30, 31-67, and 79-98 Vasodilate the Aorta" *Biochemical and Biophysical Research Communications*, Nov. 13, 1987, pp. 1540-1548, vol. 148, No. 3.

Vesely, D.L. et al. "Increased Release of the N-Terminal and C-Terminal Portions of the Prohormone of Atrial Natriuretic Factor During Immersion-Induced Central Hypervolemia in Normal Humans" *Proc Soc Exp Biol Med*, 1989, pp. 230-235, vol. 192.

Vesely, D.L. et al. "Negative Feedback of Atrial Natriuretic Peptides" *Journal of Clinical Endocrinology and Metabolism*, 1994, pp. 1128-1134, vol. 78, No. 5.

Vesely, D.L. et al. "Novel therapeutic approach for cancer using four cardiovascular hormones" *European Journal of Clinical Investigation*, 2004, pp. 674-682, vol. 34.

Vesely, D.L. et al. "Three Peptides From the Atrial Natriuretic Factor Prohormone Amino Terminus Lower Blood Pressure and Produce Diuresis, Natriuresis, and/or Kaliuresis in Humans" *Circulation*, 1994, pp. 1129-1140, vol. 90.

Vesely, D.L. et al. "Vessel Dilator Enhances Sodium and Water Excretion and Has Beneficial Hemodynamic Effects in Persons With Congestive Heart Failure" *Circulation*, 1998, pp. 323-329, vol. 98.

Vesely, D.L., "Atrial Natriuretic Peptide Prohormone Gene Expression: Hormones and Diseases That Upregulate its Expression" *IUBMB Life*, 2002, pp. 153-159, vol. 53.

Vesely, D.L., "Natriuretic peptides and acute renal failure" *Am J Physiol Renal Physiol*, 2003, pp. F167-F177, vol. 285.

Villarreal, D. et al. "Hemodynamic and Renal Effects of ProANF$_{31-67}$ in Hypertensive Rats $_{(44399)}$" *Proceedings of the Society for Experimental Biology and Medicine*, 1999, pp. 166-170, vol. 221, No. 3.

Weller, M. et al. "Predicting Chemoresistance in Human Malignant Glioma Cells: The Role of Molecular Genetic Analyses" *Int. J. Cancer (Pred. Oncol.)*, 1998, pp. 640-644.

White, R.E. et al. "Potassium channel stimulation by natriuretic peptides through cGMP-dependent dephosphorylation" *Nature*, Jan. 21, 1993, pp. 263-266, vol. 361.

Wigle, D.A. et al. "ANP secretion from small cell lung cancer lines: a potential model of ANP release" *Am J Physiol Heart Circ Physiol*, 1995, pp. H1869-H1874, vol. 268, abstract.

Winters, C.J. et al. "The N-Terminus and a 4,000-MW Peptide From the Midportion of the N-Terminus of the Atrial Natriuretic Factor Prohormone Each Circulate in Humans and Increase in Congestive Heart Failure" *Circulation*, 1989, pp. 438-449, vol. 80.

Yagoda, A. et al. "Chemotherapy for Advanced Renal-Cell Carcinoma: 1983-1993" *Seminars in Oncology*, Feb. 1995, pp. 42-60, vol. 22, No. 1.

Yang, J.C. et al. "Randomized Study of High-Dose and Low-Dose Interleukin-2 in Patients With Metastatic Renal Cancer" *Journal of Clinical Oncology*, Aug. 15, 2003, pp. 3127-3132, vol. 21, No. 16.

Yu, C.C.W. et al. "The assessment of cellular proliferation by immunohistochemistry: A review of currently available methods and their applications" *The Histochemical Journal*, Mar. 1992, pp. 121-131, vol. 24, No. 3.

Yu, M.C. et al. "Cigarette Smoking, Obesity, Diuretic Use, and Coffee Consumption as Risk Factors for Renal Cell Carcinoma" *J Natl Cancer Inst*, Aug. 1986, pp. 351-356, vol. 77.

Zeidel, M.L., "Regulation of Collecting Duct Na$^+$ Reabsorption by ANP 31-67" *Clinical and Experimental Pharmacology and Physiology*, 1995, pp. 121-124, vol. 22, abstract.

Zellner, A. et al. "Disparity in Expression of Protein Kinase C α in Human Glioma *versus* Glioma-derived Primary Cell Lines: Therapeutic Implications" *Clinical Cancer Research*, Jul. 1998, pp. 1797-1802, vol. 4.

Zips, D. et al. "New Anticancer Agents: In Vitro and In Vivo Evaluation" *In Vivo*, Jan./Feb. 2005, pp. 1-7, vol. 19, No. 1.

Bellone, M. et al. "Cancer immunotherapy: synthetic and natural peptides in the balance" *Immunology Today*, Oct. 1999, 20(10):457-462.

Gaiger, A. et al. "Immunity to WT1 in the animal model and in patients with acute myeloid leukemia" *Blood*, 2000, 96:1480-1489.

US 7,846,900 B2

CANCER TREATMENT USING C-TYPE NATRIURETIC PEPTIDE

CROSS REFERENCE TO RELATED APPLICATIONS

This application is a continuation of U.S. application Ser. No. 10/908,604, filed May 18, 2005, now U.S. Pat. No. 7,488,713; which application is a continuation-in-part of U.S. patent application Ser. No. 10/708,688, filed Mar. 18, 2004, now U.S. Pat. No. 6,943,147; which application claims the benefit of U.S. Provisional Application No. 60/320,018, filed Mar. 19, 2003.

BACKGROUND OF THE INVENTION

Cancer of the prostate is the most commonly diagnosed neoplasm in men with over 232,000 new cases estimated in the United States in 2005, i.e., 30% of all new cancer diagnoses in men. Mortality from prostate cancer remains a significant problem with current treatment(s) with an estimated 30,350 deaths from prostate cancer in 2005 making it the second leading cause of cancer death in men after lung cancer.

Lung cancer is the leading cause of cancer death in both men and women in the United States, and this same trend is seen in many other countries. In the United States in 2004 it was estimated that lung cancer accounted for 31% of cancer deaths in men and 25% of cancer deaths in women. Small-cell lung cancers account for 20% to 25% of all lung cancers. Small-cell lung cancer differs from other lung cancers in that it metastasizes very early and can rarely be cured surgically. In the current management of small-cell lung cancers the majority of patients are treated first with chemotherapy plus radiotherapy, but with this combination survival is only 20% at 3 years. There is an increased incidence of secondary cancers with the cisplatin- and cytoxan-based regimens used to treat small-cell lung cancer, and the chemotherapeutic regimens for small-cell lung cancer containing doxorubicin may induce cardiac myopathy. All the presently utilized chemotherapeutic agents for treatment of small-cell lung cancers have some side-effects, including myelosuppression. Atrial natriuretic peptides consist of a family of peptides that are synthesized by three different genes then stored as three different prohormones [i.e., 126 amino acid (a.a.) atrial natriuretic peptide (ANP), 108 a.a. brain natriuretic peptide (BNP), and 103 a.a. C-type natriuretic peptide (CNP) prohormones] (8-10). Within the 126 a.a. ANP prohormone are four peptide hormones i.e., long acting natriuretic peptide (LANP), vessel dilator, kaliuretic peptide, and atrial natriuretic peptide (ANP), whose main known biologic properties are blood pressure regulation and maintenance of plasma volume in animals and humans. The BNP and CNP genes, on the other hand, appear to each synthesize only one peptide hormone within their respective prohormones, i.e., BNP and CNP. Each of these peptide hormones circulates in healthy humans with vessel dilator and LANP concentrations being 17- to 22-fold higher than ANP, 33- to 48-fold higher than BNP and 124 to 177-fold higher than CNP.

Therefore, what is needed is a method of treating cancer that can both improve survival, lacks the side effects of current therapies, and ultimately decrease morbidity.

SUMMARY OF INVENTION

In a general embodiment, the present invention comprises a method of inhibiting the growth of cancer cells comprising the step of contacting at least one target cell with an effective amount of a peptide hormone derived from the C-natriuretic peptide (CNP) prohormone. The peptide hormone administered is derived from the CNP prohormone. In one embodiment, the target cell is chosen from the group consisting of adenocarcinomas, small cell carcinomas and squamous cell carcinoma, and the peptide hormone is administered in vivo.

In another embodiment, the invention includes a method of inhibiting the growth of cancer cells comprising the step of co-administering, to at least one target cell, an effective amount of a combination of peptide hormones derived from the ANP prohormone and a peptide hormone derived from the C-natriuretic peptide (CNP) prohormone. The combination of peptide hormones is derived from the ANP prohormone and a peptide hormone derived from the C-natriuretic peptide (CNP) prohormone is selected from the group consisting of atrial natriuretic peptide, long acting natriuretic peptide, vessel dilator, kiliuretic peptide, and C-natriuretic peptide. In another embodiment the target cell is chosen from the group consisting of adenocarcinomas, small cell carcinomas and squamous cell carcinoma, and the combination of peptide hormones is administered in vivo.

The present investigation is a new therapeutic approach that has none of the side effects of current cancer therapeutic agents. This approach is to utilize peptide hormones made mainly in the atria of the heart called atrial natriuretic peptides. These peptide hormones have recently been found to have significant anticancer effects on human breast and pancreatic adenocarcinomas as well as small-cell and squamous cell lung carcinomas.

The present investigation incorporates the atrial peptides made by all three genes within the heart, i.e., the above four peptide hormones plus BNP and CNP. When the four peptide hormones from the ANP gene were found in dose-response studies to cause a significant decrease in the number of human prostate adenocarcinoma cells (i.e., up to 97.4% within 24 hours), it was investigated whether the mechanism(s) of this decrease in the number of human prostate adenocarcinoma and small-cell carcinoma cells and the ability of these peptides to inhibit further proliferation of these cancer cells after their decreased number was owing to inhibition of DNA synthesis. It was then determined whether their intracellular mediator cyclic GMP could reproduce their effects on human prostate adenocarcinoma cells and DNA synthesis. The inventors further examined the prostate adenocarcinoma cells to determine if they have natriuretic peptide (NPR)-A and -C receptors to mediate these peptide hormones effects since natriuretic peptide receptors have never been demonstrated on prostate cancer cells.

In the present invention, these cardiovascular peptide hormones decrease the number of human small-cell lung cancer cells showing that these peptides are a good addition to the therapeutic regimen for small-cell lung cancers, as they do not cause myleosuppression, secondary tumours, cardiac myopathy or any known side-effect of cancer chemotherapeutic agents. Thus, their use allows for the current anticancer chemotherapeutic agents to be used in a lower dose(s) to obtain the same effect. Utilizing one or more of these peptide hormones might also allow for a dose-escalation of currently used chemotherapeutic agents as an important strategy for overcoming drug resistance. Thus, this dose-escalation is less than the present escalation of current chemotherapeutic agents, as the peptide hormones of the current investigation would decrease the number of cancer cells as demonstrated in the present invention before this dose-escalation would begin. With less cells to kill, as the vessel dilator kills 92% of the cells within 24 hours, this dose escalation does not have to increase as much as in current clinical trials, thereby achieving higher complete remission rates and increasing cures with less side-effects, as the total dose(s) of the chemotherapeutic agents to achieve cure is less if the above peptide hormones (without current anticancer agents' side-effects) are given first.

These peptide hormones, which circulate normally in the human body, have no known cytoxic effects on normal cells and only one known side-effect. This side-effect, i.e. hypotension, has only been observed with ANP and BNP and never with the vessel dilator, LANP, or kaliuretic peptide. These last three peptide hormones with the best safety profile also decrease adenocarcinoma cells in vitro the most, small-cell lung cancer cells in vitro the most (present investigation), and decrease adenocarcinoma tumour volume in vivo the most out of the ANPs. Presently, utilized chemotherapy very commonly causes toxicity in the form of nausea, vomiting, alopecia, and myelosuppression. None of these toxicities occur with the ANP hormones.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
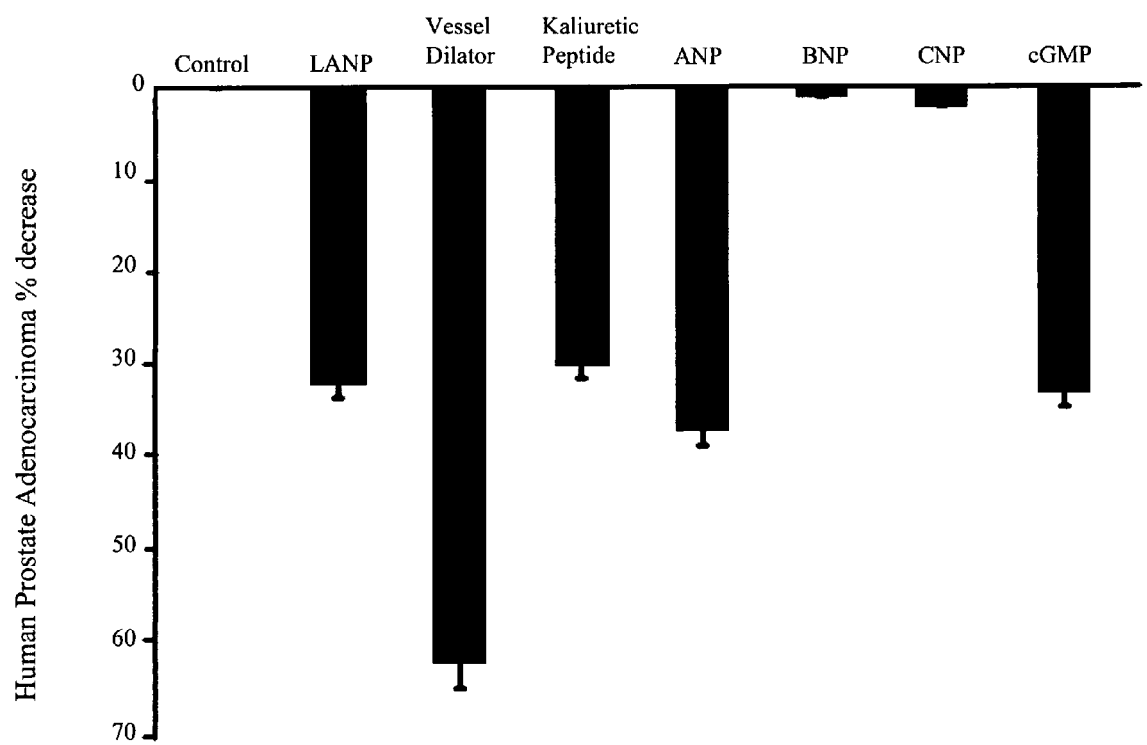
FIG. 1. Decrease in human prostate adenocarcinoma cells after 24 hour exposure to 1 µM of long acting natriuretic peptide (LANP), vessel dilator, kaliuretic peptide, atrial natriuretic peptide (ANP), brain natriuretic peptide (BNP) and C-type natriuretic peptide (CNP).

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The present invention is the first evaluation of whether prostate adenocarcinomas cells contain natriuretic peptide receptors. Both the NPR-A and NPR-C receptors were present in human prostate adenocarcinoma cells. This knowledge helps to explain brain natriuretic peptide (BNP) and C-natriuretic peptide (CNP)'s decreased biologic effects in these cancer cells at their 1 µM concentrations. ANP binds to both the NPR-A and C-receptors with a higher affinity than BNP or CNP. The binding to the NPR-A receptor is ANP>BNP>>CNP while binding to the NPR-C receptor is ANP>CNP>BNP. Thus, one needs significantly more of BNP and CNP to cause the same effects observed with ANP and that is why they have no effects when compared at the same concentration where ANP first has anticancer effects.

Although prostate cancer is curable with surgery if it is detected and removed at an early stage, unfortunately is not always detected when it is surgically curable. With current treatment with anti-androgens, etc. it is still the second leading cause of cancer death in men after lung cancer. With an estimated 30,350 prostate cancer deaths expected to occur this year (2005) with surgery and current cancer chemotherapy plus anti-androgens there is an urgent need to develop new approaches to therapy of prostate cancer. The present investigation details not only one but four new potential therapies which kill up to 97.4% of human prostate cancer cells within 24 hours. These peptide hormones which circulate normally in the human body have no known cytoxic effects to normal cells and only one known side effect. This side effect, i.e., hypotension, has only been observed with ANP and BNP and never with vessel dilator, LANP, or kaliuretic peptide in human or animal subjects. These last three peptide hormones with the best safety profile also decrease breast and pancreatic adenocarcinoma cells in vitro the most and decrease adenocarcinoma tumor volume in vivo the most of the atrial natriuretic peptides. There was no hypotension in the animals where these peptide hormones decreased up to 50% of the tumor volume of human pancreatic adenocarcinomas in vivo in one week. Presently utilized chemotherapy commonly causes toxicity in the form of nausea, vomiting, alopecia, and myelosuppression. None of these toxicities occur with the atrial natriuretic peptide hormones.

Example I

Prostate Adenocarcinoma Cells

All four of the peptide hormones synthesized by ANP gene, i.e., LANP, vessel dilator, kaliuretic peptide and ANP had very significant ($P<0.001$) effects at their 1 mM concentrations decreasing the number of cancer cells by 87% to 97.4% within 24 hours.

Figure 2A:
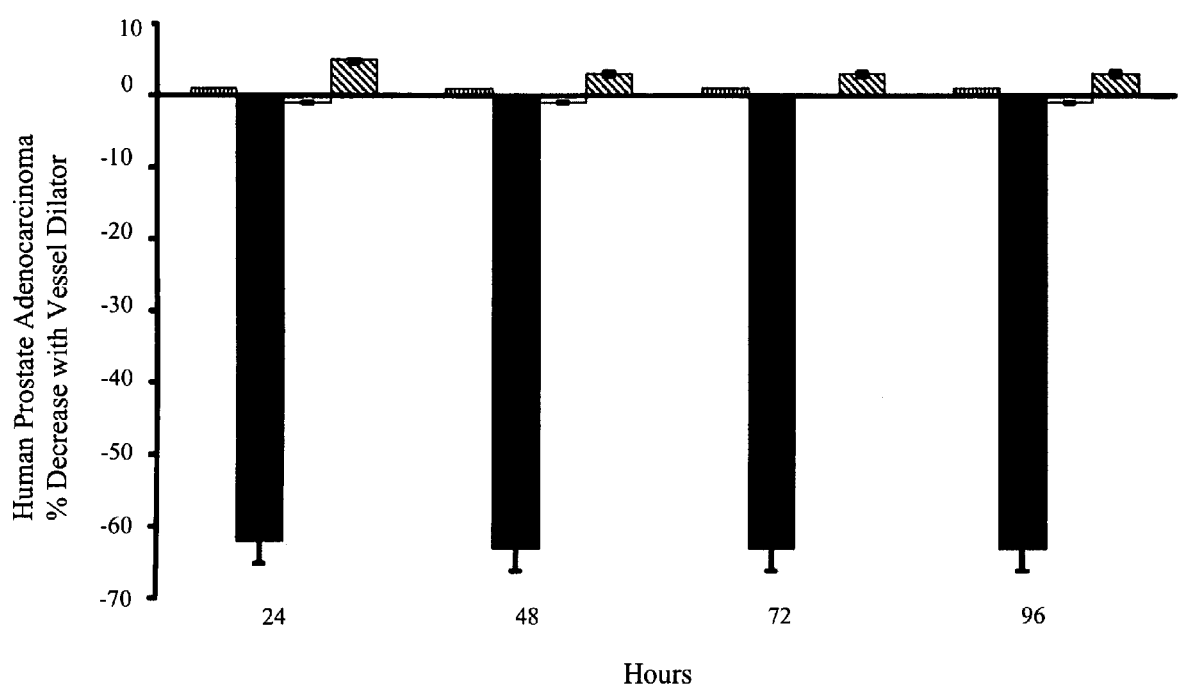
FIGS. 2A-2D are graphs showing the specific decrease in human prostate cancer cell number with 1 µM concentrations of these peptide hormones.
Figure 3:
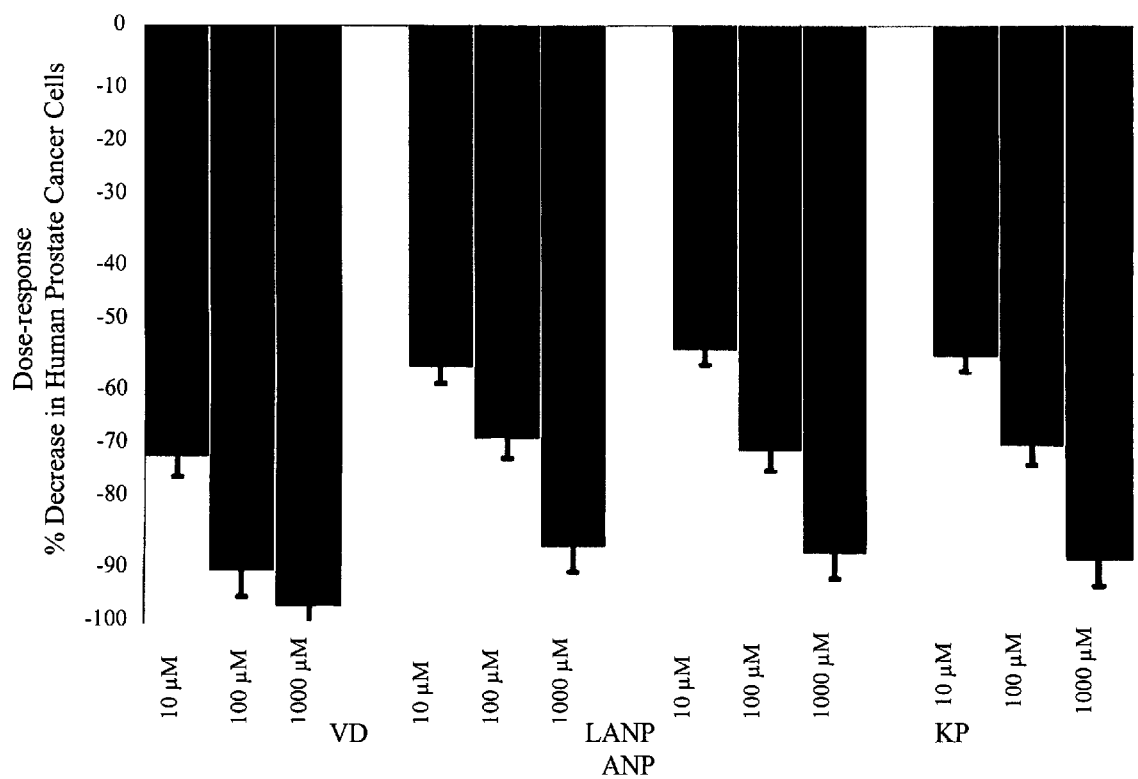
FIG. 3. Dose-response of vessel dilator (VD), long acting natriuretic peptide (LANP), kaliuretic peptide (KP) and atrial natriuretic peptide (ANP)'s anticancer effects on human prostate adenocarcinoma cells.

Vessel dilator was the most potent of these peptide hormones in decreasing the number of the human prostate cancer cells at each of the respective concentrations of these peptide hormones (FIG. 3). Vessel dilator had significant (P<0.001) effects within 24 hours at its 1 µM concentration (62% decrease in number of prostate adenocarcinoma cells) and inhibited any further proliferation of the prostate cancer cells from 24 to 96 hours (P<0.001; FIG. 2A). In the dose-response curves of the present investigation, when vessel dilator concentration was increased 10-fold and 100-fold (i.e., 10 and 100 µM), vessel dilator decreased the number of human cancer cells 72% and 91% within 24 hours (FIG. 3). When vessel dilator concentration was increased to 1 mM, 97.4% of the cancer cells were killed in 24 hours i.e., only three cancer cells (3±2.74 cells) that had not been killed (FIG. 3). Thus, vessel nearly eliminated all of the human cancer cells within 24 hours. In several of the fields there were no cancer cells at all, i.e., vessel dilator had killed 100% of the cancer cells within these fields in 24 hours. Vessel dilator also decreased human pancreatic and breast adenocarcinomas in vitro the most and small-cell and squamous cell lung cancer cells in vitro the most and decreased human pancreatic adenocarcinoma tumor volume the most in vivo suggesting that it has the most significant anticancer properties of these peptide hormones.

The other three peptide hormones synthesized by the ANP gene effects on decreasing the number of prostate adenocarcinoma cells were significant, however. When the concentrations of LANP, kaliuretic peptide, and ANP were increased in dose-response curves to 1 mM, they caused a very significant 87% to 89% decrease in the number of human prostate adenocarcinoma cells within 24 hours. There appears to be a difference in these peptide hormones' ability to decrease cancer cell number depending upon the type of cancer. Kaliuretic peptide (1 µM), for example, ability to decrease the number of prostate adenocarcinoma cells at 24 hours (30% decrease) although similar to its effect (30%) on small-cell lung cancer cells was not as good (37% decrease) as with human pancreatic adenocarcinoma cells. It should be noted that there was no decrease in the number of cells when examined immediately after addition of the respective peptide hormones indicating that the data obtained was not due to artifact. It is also important to note that after 24 hours of incubation with the four peptide hormones that cellular debris was present suggesting that cellular necrosis was occurring.

The effect of these four peptide hormones on decreasing the number of human pancreatic cancer cells was very specific as evidenced by the antibody studies where the addition of the respective antibodies to the peptide hormones resulted in a maximum of only 2% of the cancer cells being decreased (FIG. 2). This maximum 2% was seen only with the kaliuretic peptide antibody plus kaliuretic peptide and only at one time period with no decrease whatsoever at 72 and 96 hours with kaliuretic peptide plus its antibody. With each of the other three antibodies plus their respective peptide the decrease was 0 to 1% which is significantly (P<0.0001) different than the peptide alone where significant decreases occurred. Since the decrease in cancer cell number secondary to these peptide hormones could be completely blocked by their respective antibodies this indicates that the peptides (rather than some other factor) were specifically the cause of the decrease in human prostate cancer cell number. The respective antibodies alone caused a slight but insignificant increase in cancer cell number (FIG. 2). The antibodies, thus, would not be useful to treat prostate adenocarcinomas as opposed to the data of the present investigation demonstrating an 87% to 97.4% decrease in cancer cell number within 24 hours with the four peptide hormones themselves.

Figure 4:
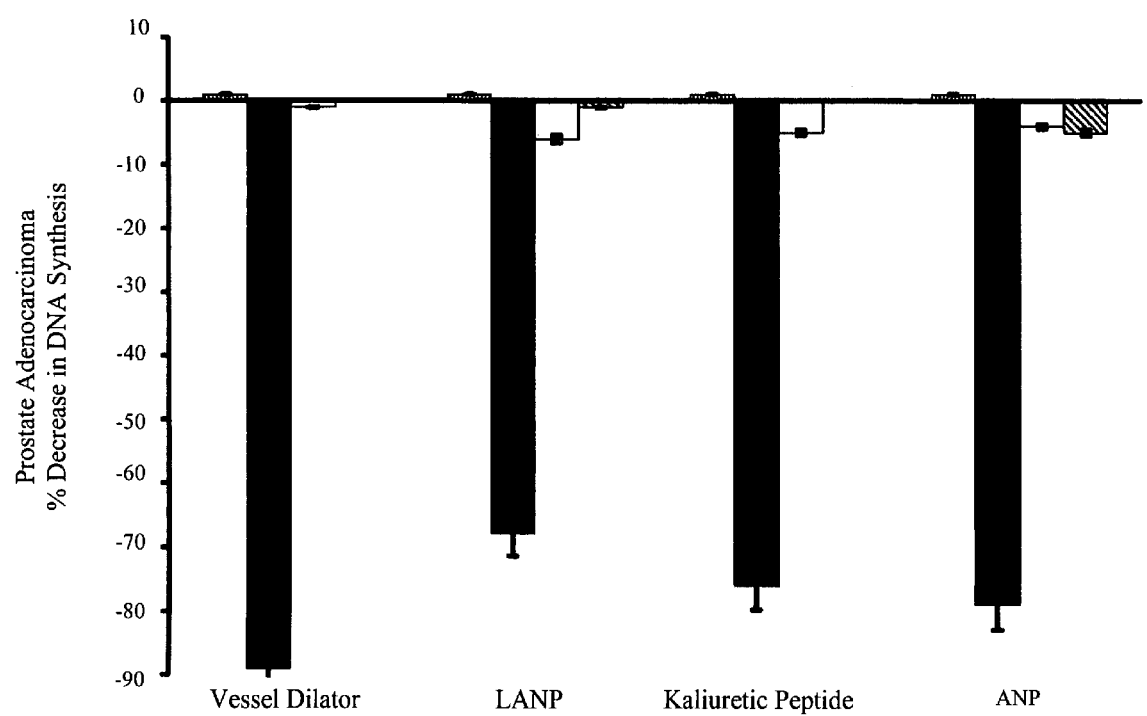
FIG. 4. Specific decrease in DNA synthesis by vessel dilator, long acting natriuretic peptide (LANP), kaliuretic peptide, and atrial natriuretic peptide (ANP).

Each of the four peptide hormones from the ANP prohormone inhibited 68% to 89% of the amount of DNA synthesis in the human prostate adenocarcinoma cells. The present investigation demonstrated that the DNA synthesis-inhibiting properties of these peptide hormones were directly due to the peptide hormones themselves as when their specific antibodies were incubated with the peptide hormones the antibodies completely blocked these four peptide hormones ability to decrease cancer cell DNA synthesis (FIG. 4). The antibodies by themselves (FIG. 4) did not significantly block DNA synthesis. These findings suggest that one important mechanism of action of these peptide hormones to inhibit cancer cell number and their proliferation is via their ability to inhibit DNA synthesis. This finding is similar to the ability of these peptide hormones to inhibit DNA synthesis in human pancreatic adenocarcinoma cells and human breast adenocarcinoma cells.

With respect to the mechanism of how these peptide hormones inhibit DNA synthesis, one of the second messengers of their biologic effects, i.e., cyclic GMP was found using 8-bromo cyclic GMP (1 mM) to inhibit DNA synthesis 87% in the human prostate cancer cells. Cyclic GMP's mimicking the effects of these peptide hormones on DNA synthesis in the same cells suggests that cyclic GMP is one of the mediators of these peptide hormones' ability to inhibit DNA synthesis in prostate adenocarcinoma cells. Further evidence that the cyclic GMP inhibition of DNA synthesis in prostate cancer cells may be important for these peptide hormones anticancer growth effects is that when cyclic GMP was infused subcutaneously for a week in athymic mice with human pancreatic adenocarcinomas, it inhibited 95% of the growth of the human pancreatic adenocarcinoma compared to placebo-treated adenocarcinomas.

The cell line (ATCC number CRL-1435; PC-3) of human prostate adenocarcinoma cells was derived in 1979 by M. E. Kaighn et al. from a grade IV prostate adenocarcinoma from of a 62 year old Caucasian man. These cells, when injected into athymic mice, form tumors within 21 days.

Culture of the Prostate Adenocarcinoma Cells

Propagation of these cells was in Ham's F1K medium with 2 mM/L-glutamine adjusted with addition of 1.5 g/L sodium bicarbonate, 90%; and heat-inactivated 10% fetal bovine serum at a temperature of 37° C. as recommended by the ATCC. Cells were dispensed into new flasks with subculturing every 6-8 days. The growth medium was changed every three days.

After the prostate adenocarcinoma cells were subcultured for 24 hours they were then seeded to coverslips in 24 well plates with 1 mL of the above Ham's F12K media. After 24 hours, wells were washed twice with phosphate buffered saline to remove the fetal bovine serum. Removal of serum was done to completely remove all variables (EGF, etc.) present in serum in order that interpretation of any data obtained would be straightforward. After 24 hours of serum deprivation, media volume was reduced to 250 µL per well with or without the respective peptide hormones in dose response curves with concentrations up to and including 1 mM (1% of this volume). Human prostate adenocarcinoma cells were then incubated for various periods of time. The number of prostate adenocarcinoma cells were then counted with a cell counter evaluating ten fields of the microscope slide at 40× along the X-axis. This evaluation was repeated on six separate occasions with the number of prostate adenocarcinoma cells reflecting 60 observations for each group, i.e., 60 observations for controls and 60 observations for each of the six groups with respective peptide hormones.

Specificity of These Peptide Hormones to Decrease the Number of Human Prostate Adenocarcinoma Cells.

To determine if the decrease in number of human pancreatic adenocarcinoma cells was specific, these peptide hormones (1 μM) and their specific antibodies (5 μM) were incubated together for 24, 48, 72, and 96 hours. Both the peptide hormones and their antibodies were from Phoenix Pharmaceuticals, Inc., Belmont, Calif. The antibodies (5 μM) were also incubated alone (i.e., without the peptide hormones) at each of the above time points.

Determination of DNA Synthesis.

To investigate whether these peptide hormones were inhibiting DNA synthesis, bromodeoxyuridine (BrdU) incorporation into the prostate adenocarcinoma cells was utilized. DNA synthesis and doubling of the genome take place during the synthetic or S phase (32,33). Bromodeoxyuridine is a thymidine analog incorporated into nuclear DNA during the S phase of the cell cycle. After 24 hours in culture with 1 μM of LANP, vessel dilator, kaliuretic peptide, ANP, BNP, or CNP, respectively, or with no peptide hormone (i.e., control), BrdU in a final concentration of 10 μM in the cell culture medium was added for 45 minutes—which is the time in which the cells are in the logarithmic phase of cell proliferation. For immunohistochemistry, a BrdU in situ detection kit was utilized.

The incorporation of the BrdU stain into the nucleus was counted using a Nikon Inverted Diaphot-TMD Microscope (Tokyo, Japan). The number of stained nuclei were compared in the six peptide hormone groups to the positive control group. To investigate DNA synthesis, BrdU incorporation by immunochemistry has been demonstrated to be equally good as $^3$H-thymidine incorporation and has the advantage that it provides high resolution.

Cyclic GMP Effects on DNA Synthesis.

Cyclic GMP is one of the known mediators of the previously described biologic effects of these peptide hormones. All four of these peptides synthesized by the ANP gene-induced vasodilations of vasculature are mediated by increased cyclic GMP concentrations via enhancing guanylate cyclase activity. The inventors have previously shown that each of these peptide hormones increase cyclic GMP while simultaneously dilating vasculature. 8 bromo-cyclic GMP reproduces these vasodilatory effects. For the present investigation of part of the mechanism of these peptide hormones' ability to inhibit DNA synthesis in prostate adenocarcinoma cells, 8-bromoguanosine 3',5'-cyclic monophosphate was utilized. 8-bromo cyclic GMP is a cell-permeable analog of cyclic GMP.

ANP Receptors in Human Prostate Adenocarcinoma Cells.

Prostate cancers have never been examined to determine if they have natriuretic receptors. When it was found that these ANPs decreased the number of human prostate adenocarcinoma cells, it was then evaluated whether prostate cancer cells have ANP receptors to mediate these effects. Western blots of the natriuretic peptide receptors (NPR) A- and C- were performed as follows:

Western Blotting. Seventy-five micrograms of protein extract from human prostate adenocarcinoma cells, measured by using the bicinchonic acid (BCA) protein assay kit was loaded onto each lane of a Criterion Precast 7.5% Tris-HCl gel, separated by electrophoresis (200 volts for 60 min), and then transblotted onto a nitrocellulose membrane for 75 min at 100 volts in Towbin buffer. Blots were blocked for 1 hour at room temperature in a 5% solution of dry milk, washed×3 with Tris buffered saline, and then incubated for 1 hour in a 5% solution of bovine serum albumin in Tris-buffered saline that contained a 1:4,000 dilution of A035 polyclonal antibody directed against the COOH terminus of the NPR-A receptor protein or containing Tris-buffered saline with a 1:1,000 dilution of antibody to the NPR-C receptor. After being washed×4 with Tris-buffered saline, the membranes were incubated for 1 hour at room temperature in a solution of dry milk with a 1:6,000 and 1:3,000 dilutions of goat anti-rabbit IgG antibody for NPR-A and NPR-C receptors, respectively. After three washings with Tris-buffered saline, the bands were identified by enhanced chemiluminescence reagents and visualized in a luminescent image analyzer. Specificity was revealed by the presence of a signal in rat lung (positive control) and absence of a signal with normal rabbit serum, rabbit IgG, and after preabsorption of the NPR-A antibody with NPR-A protein or preabsorption of the NPR-C antibody with NPR-C protein. Monoclonal anti-B-actin antibody was used as a loading control.

Decrease in Number of Human Prostate Adenocarcinoma Cells by Four Peptide Hormones Synthesized by the ANP Gene.

The number of prostate adenocarcinoma cells after 24 hours without the addition of any of the peptide hormones averaged 89±2 cells per high-powered field when ten fields of the coverslip were evaluated at ×40 along the x-axis. This evaluation was repeated on six separate occasions with the above number reflecting sixty observations of the number of control prostate adenocarcinoma cells and sixty observations of each of the six groups with addition of one of the peptide hormones (FIG. 1). The decrease in prostate cancer cells was significant at P<0.001 with vessel dilator, P<0.01 with ANP, and P<0.05 with kaliuretic peptide and LANP when evaluated by repeated analysis of variance (ANOVA). There was no significant decrease in prostate cancer cell number secondary to BNP or CNP when evaluated by ANOVA. The decrease in number of human prostate cancer cells secondary to vessel dilator was significantly greater (P<0.05) than the decrease secondary to any of the other natriuretic peptides when evaluated by ANOVA. Cyclic GMP's (cGMP) (1 μM) decrease in prostate adenocarcinoma cells was significant at P<0.05 when evaluated by ANOVA.

The addition of 1 μM of long acting natriuretic peptide (LANP) for 24 hours decreased the number of human prostate cancer cells to 60±3 i.e., a 32% decrease (P<0.05) in the number of prostate adenocarcinoma cells with the LANP (FIG. 1). Vessel dilator at 1 μM for 24 hours had an even more dramatic decrease (62%; P<0.001) in the number of the human prostate adenocarcinoma cells (FIG. 1). Vessel dilator decreased the number of lung cancer cells from 89±2 cells to 33±3. Kaliuretic peptide at 1 μM for 24 hours decreased the number of human prostate adenocarcinoma cells 30% (P<0.05), i.e., to 62±3 prostate cancer cells (FIG. 1).

The number of human prostate adenocarcinoma cells in culture decreased 37% (P<0.05) when exposed to atrial natriuretic peptide (1 μM) for 24 hours (FIG. 1). Brain natriuretic peptide and CNP, each at 1 μM, only decreased the number of human prostate adenocarcinoma cells 0.8% and 1%, respectively, after 24 hours of incubation (not significant). Thus, with respect to their ability to inhibit the growth of human prostate cancer cells when these cells were exposed to identical concentrations of these six peptide hormones for 24 hours, vessel dilator>ANP>kaliuretic peptide>LANP>CNP>BNP. When the number of cells was examined immediately after the incubation of the respective peptide hormones within the cells, there was not any decrease in the number of cancer cells. In the wells with decreased number of cells secondary to the cardiac hormones, there was evidence of cellular debris.

Specificity of the Ability of These Peptide Hormones to Decrease the Number of Human Pancreatic Adenocarcinoma Cells.

To determine if the significant effects of these peptide hormones to decrease the number of human prostate adenocarcinoma cells were specific the inventors utilized these peptides hormones specific antibodies in a 1:5 concentration of peptide hormone to their respective antibody. As shown in FIGS. (2A) vessel dilator, (2B) long acting natriuretic peptide (LANP), (2C) kaliuretic peptide, and (2D) atrial natriuretic peptide (ANP)'s anticancer effects compared to placebo-treated human prostate adenocarcinoma cells at 24, 48, 72, and 96 hours were significant at $P<0.001$ compared to placebo when evaluated by repeated analysis of variance (ANOVA). The addition of their respective specific antibodies (5 $\mu$M) blocked these peptide hormones' anticancer effects which was significant at $P<0.001$ when evaluated by repeated measures of ANOVA at 24, 48, 72, and 96 hours of incubation. The addition of the respective antibody alone resulted in a slight increase in cancer cell number that was not significant when evaluated by ANOVA.

Figure 2B:
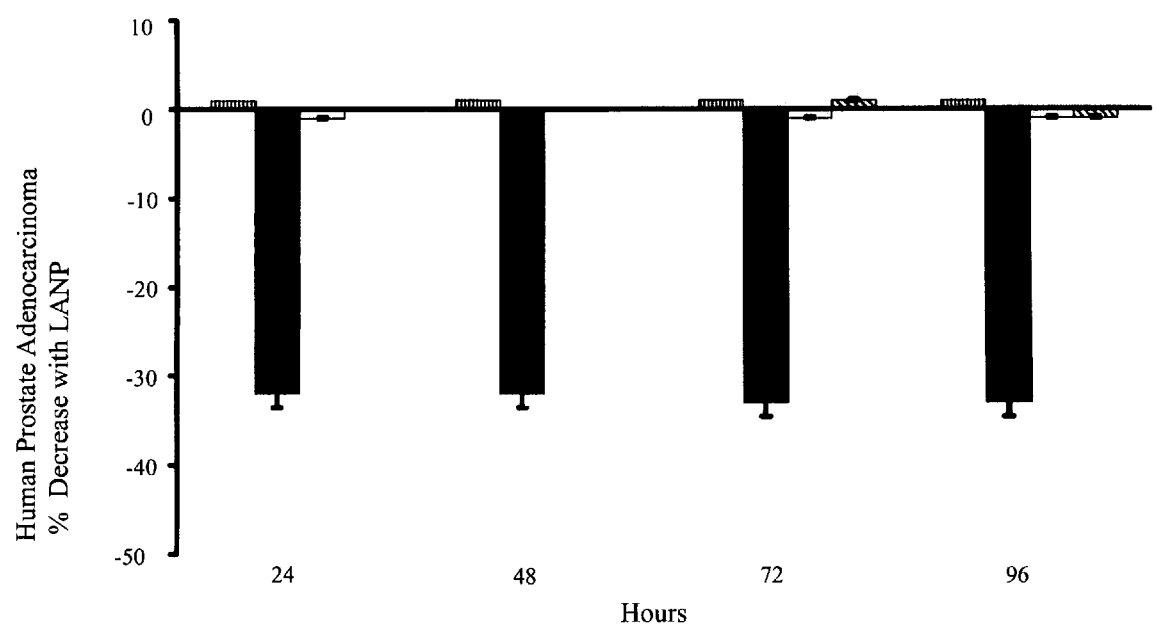
Figure 2C:
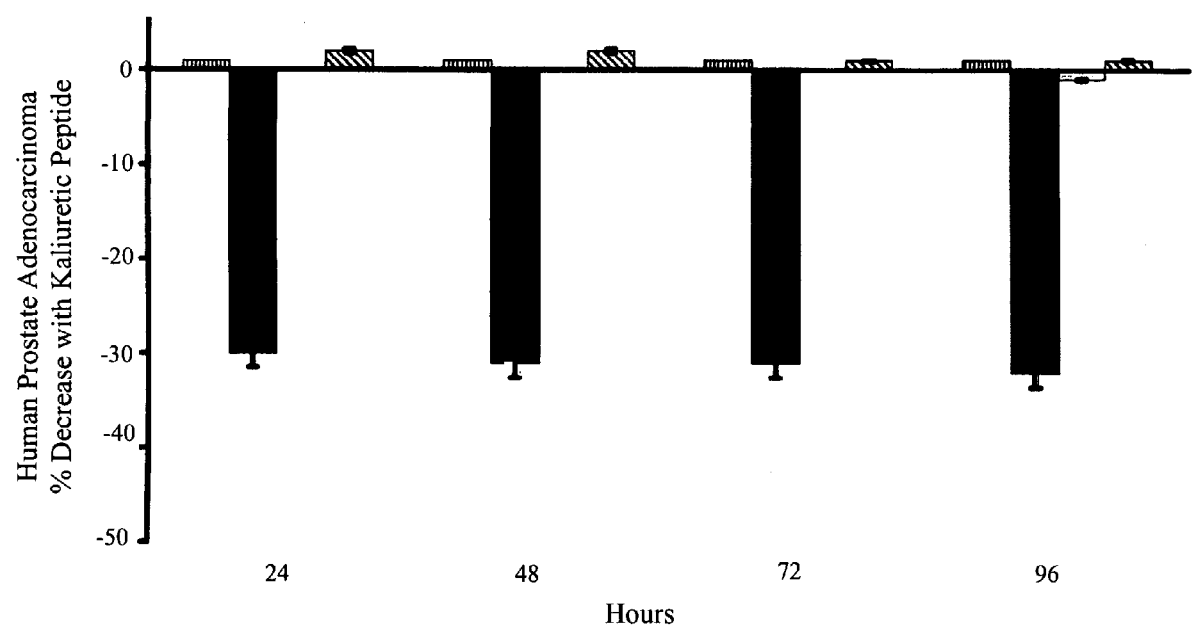
Figure 2D:
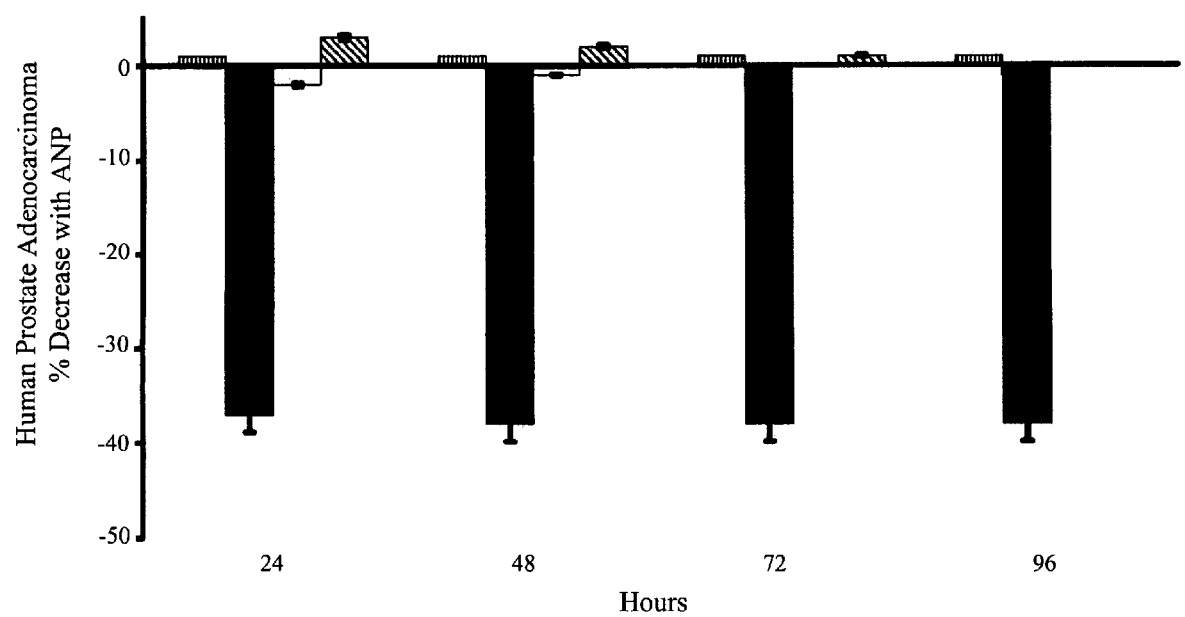

When these peptide hormones (each at 1 $\mu$M) were incubated with their specific antibodies (5 $\mu$M) the decrease in cancer cell number secondary to vessel dilator alone of 62% was reduced to 1% only (FIG. 2A). There was also only a 1% decrease in cell number with LANP plus its antibody (FIG. 2B). Kaliuretic peptide plus its antibody resulted in a 0.4% decrease versus a 30% decrease with kaliuretic peptide alone (FIG. 2C). These antibodies studies also indicated that ANP's effects were specific with the 37% decrease in cell number with ANP alone decreased to 2% when its antibody was added (FIG. 2D). The addition of specific antibody blocked each of these peptides ability to decrease cancer cells at $P<0.0001$.

When these specificity experiments were extended to 48, 72, and 96 hours of incubation of antibody plus peptide hormones, for vessel dilator plus antibody (FIG. 2A) the decrease in number of cancer cells was 1%, 0%, and 1%, respectively ($P<0.0001$). LANP plus its antibody resulted in 0%, 1%, 1% decrease in cancer cells (FIG. 2B) at 48, 72, and 96 hours. With kaliuretic peptide plus its antibody there was a 0%, 0%, and 1% decrease in prostate cancer cell number at 48, 72, and 96 hours, respectively (FIG. 2C). When ANP's antibody plus ANP were incubated for 48, 72, and 96 hours there was a 1%, 0%, and 0% decrease in prostate cancer cells (FIG. 2D).

When the antibodies alone (same concentration, i.e., 5 $\mu$M) were incubated for 24 hours without the addition of any of the peptide hormones, the vessel dilator antibody resulted in a 5% increase (rather than decrease) in prostate cancer cell number while the ANP antibody resulted in a 3% increase in prostate adenocarcinoma cells. With the LANP and kaliuretic peptide antibodies alone for 24 hours there was a 0.1% decrease and 2% increase, respectively. Thus, there was no significant decrease in cancer number with the antibodies alone, but rather 3 of the 4 antibodies caused an increase in cancer cell number within 24 hours. When the antibody alone experiments were extended for 48, 72, and 96 hours there was a 3% increase in cancer cells at each time period with vessel dilator (FIG. 2A) with a 0%, 1% increase, and 1% decrease respectively at these time periods with LANP (FIG. 2B). When the kaliuretic peptide antibody alone was incubated for 48, 72, and 96 hours there was a 2%, 1%, and 1% increase, respectively (FIG. 2C), while with ANP antibody alone there was a 2%, 1%, and 0% increase at these time points (FIG. 2D).

Decreased Cellular Proliferation after Initial Decrease in Human Prostate Adenocarcinoma Cell Number.

When the prostate adenocarcinoma cells were exposed for longer periods of time e.g., 48, 72, and 96 hours to vessel dilator, LANP, kaliuretic peptide, ANP, BNP, and CNP each at 1 $\mu$M, there was a inhibition of proliferation of the prostate cancer cells after the decrease in the number of these cancer cells at 24 hours by the peptide hormones from the ANP gene (FIG. 2). Thus, when exposed to vessel dilator, LANP, kaliuretic peptide and ANP for 48 hours the inhibition of the number of cancer cells compared to untreated human prostate adenocarcinoma cells was 63% ($P<0.001$), 32%, 31% and 38% ($P<0.05$ for these three peptides), respectively (FIG. 2). At 72 hours and 96 hours, the decrease in number of prostate adenocarcinoma cells secondary to vessel dilator was 63% at both time periods ($P<0.001$, FIG. 2). At both 72 and 96 hours, the number of prostate adenocarcinoma cells was reduced 33% by LANP ($P<0.05$ for both) compared to untreated prostate adenocarcinoma cells at these time periods (FIG. 2B). At 72 and 96 hours, the number of cancer cells with kaliuretic peptide present was decreased by 31% and 33%, respectively, ($P<0.05$ for each) (FIG. 2C). The number of human prostate cancer cells both at 72 and 96 hours decreased 38% secondary to ANP ($P<0.05$ for both) (FIG. 2D). Thus, proliferation was inhibited by these peptide hormones for three days after the initial decrease in cell number in the first 24 hours (FIG. 2). There was no significant decrease in human prostate adenocarcinoma cancer number secondary to BNP or CNP (each at 1 $\mu$M) at 48, 72, or 96 hours. Thus, at 48, 72, and 96 hours the decrease in prostate cancer cells was 1%, 1%, and 1%, respectively with BNP while the decrease secondary to CNP was 2%, 1.5%, and 1%, respectively.

Dose-Response Studies.

Dose response studies utilizing 10, 100 and 1000-fold higher concentrations for 24 hours revealed that with each increase in the concentrations of the four peptide hormones synthesized by the ANP gene there was a further decrease ($P<0.05$) the number of prostate cancer cells (FIG. 3). At each increasing concentration of these four peptide hormones there was a significantly ($P<0.05$) increased decrease in number in prostate cancer cells when evaluated by repeated measures of ANOVA. At their 1 mM concentration these peptide hormones decreased 87 to 98% of the prostate cancer cells ($P<0.001$ compared to control) when evaluated by repeated measures of ANOVA. Vessel dilator caused the same decrease as the other peptide hormones at a 10-fold lower concentration as observed in FIG. 3.

Vessel dilator which decreased the number of human prostate adenocarcinoma cells 63% at 1 $\mu$M further decreased the number of cancer 72% at 10 $\mu$M, 91% at 100 $\mu$M and 97.4% at 1 mM when incubated for 24 hours (FIG. 3). Thus, vessel dilator at 1 mM eliminated almost all of the human prostate adenocarcinoma cells within 24 hours (i.e., there were only 3±2.24 (5D) cells left with several of the fields that were examined having no cancer cells whatsoever still alive). Long acting natriuretic peptide (LANP) which decreased 32% of the prostate cancer cells at its 1 $\mu$M concentration decreased the number of cancer cells 57%, 69%, and 87% at its 10 $\mu$M, 100 $\mu$M, and 1 mM concentrations, respectively (FIG. 3). Kaliuretic peptide caused a 54%, 71%, and 88% decrease in prostate cancer cell number when its 10 $\mu$M, 100 $\mu$M, and 1 mM concentrations. ANP decreased the number of prostate cancer cells 55%, 70%, and 89% at its 10 $\mu$M, 100 $\mu$M, and 1 mM concentrations (FIG. 3). Thus, at their 1 mM concentrations these peptide hormones decreased 87 to 98% of the prostate cancer cells within 24 hours (FIG. 3).

Cyclic GMP Decreases Prostate Adenocarcinoma Cell Number.

Cyclic GMP at 1 $\mu$M decreased the number of human prostate cancer cells 33% at 24 hours (FIG. 1). The decrease in number of human prostate adenocarcinoma cells at 48, 72, and 96 hours was 35% at each time period, respectively, with 1 μM of cyclic GMP (P<0.05 at all time points compared to control). Dose response curves with cyclic GMP revealed that at 10 μM, 100 μM, and 1 mM of 8-bromo cyclic GMP the number of prostate cancer cells decreased 57%, 66%, and 84%, respectively.

Inhibition of DNA Synthesis by Four Peptide Hormones.

To help determine the mechanism of the prostate adenocarcinoma cells' decrease in number and decreased cellular proliferation by the above four peptide hormones, the inventors next investigated whether their effects were due to an inhibition of DNA synthesis as they have been demonstrated to decrease DNA synthesis in pancreatic and breast adenocarcinoma cells. Vessel dilator, LANP, kaliuretic peptide and ANP each at their 1 μM concentrations inhibited DNA synthesis when incubated with human prostate cancer cells for 24 hours by 89%, 68%, 76% and 79%, respectively (P<0.001 for each) (FIG. 4). There was not any significant decrease in DNA synthesis in the prostate cancer cells secondary to BNP or CNP at 1 μM (i.e., 4 and 5% decrease) (FIG. 4).

The 68 to 89% decrease in DNA synthesis secondary to these four peptide hormones (FIG. 4) (each at 1 μM) was significant (P<0.001) compared to control (i.e., untreated) cells and compared to DNA synthesis when the peptide hormones specific antibodies (5 μM) were added to the peptide hormones (P<0.001) when evaluated by repeated measures of analysis of variance (ANOVA). These peptide hormones' antibody alone did not significantly affect DNA synthesis when evaluated by repeated measures of ANOVA.

To determine if the decreases in DNA synthesis were specifically due to the respective peptide hormones of this investigation, the peptide hormones (each at 1 μM) plus their respective antibodies (5 μM) were investigated for their ability to inhibit DNA synthesis. When vessel dilator antibody was added with vessel dilator there was only a 1% decrease in DNA synthesis versus an 89% decrease in DNA synthesis with vessel dilator alone (FIG. 4). The vessel dilator antibody alone caused 0% decrease in DNA synthesis (FIG. 4). The LANP antibody plus LANP resulted in a 6% decrease in DNA synthesis while the LANP antibody alone caused a 1% decrease in DNA synthesis (FIG. 4). Kaliuretic peptide antibody plus kaliuretic peptide decreased DNA only 5% versus a 76% decrease in DNA synthesis with kaliuretic peptide alone (P<0.01). The kaliuretic peptide antibody alone caused no (0%) decrease in DNA synthesis (FIG. 4). ANP plus ANP antibody resulted in a 4% decrease in DNA synthesis versus a 79% decrease in DNA synthesis with ANP alone. When the ANP antibody was utilized by itself there was a 5% decrease in DNA synthesis (FIG. 4). These peptide hormones effects on DNA synthesis are, thus, very specific and definitely related to the peptide hormones themselves.

Cyclic GMP Inhibits DNA Synthesis in Human Prostate Cancer Cells.

To help define the mechanism(s) for these peptide hormone's ability to decrease DNA synthesis, one of the known mediators of these peptides biologic effects, i.e., cyclic GMP was investigated to determine if it could inhibit DNA synthesis in these same prostate cancer cells. 8-bromo cyclic GMP decreased DNA synthesis in prostate adenocarcinoma cells by 56% (P<0.01) at its 1 μM concentration (FIG. 4).

NPR-A and -C Receptors are Present in Human Prostate Cancer Cells.

Figure 5:
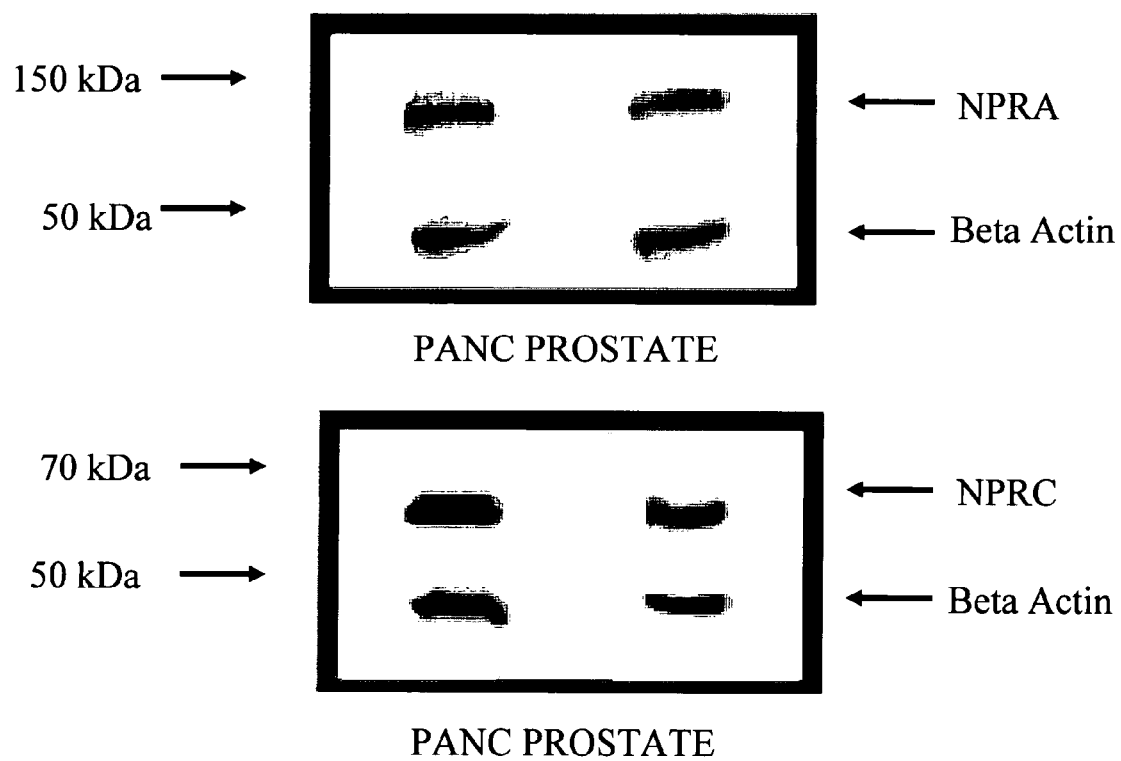
FIG. 5. Natriuretic peptide receptors (NPR) A- and C-receptors are present in human prostate cancer cells.

Prostate adenocarcinoma cancer cells have never been evaluated to determine whether they have NPR-A and/or -C receptors. When the human prostate adenocarcinoma cells were evaluated by Western blots, the NPRA- and C-receptors were demonstrated to be present (FIG. 5).

Western blot analysis with 1:4,000 dilution of A035 polyclonal antibody directed against the COOH terminus of the natriuretic peptide A-receptor (NPR-A) and 1:1,000 dilution of antibody to the NPR-C receptor. The upper graph demonstrates the positive rat lung control (PANC) for the NPR-A receptor and NPR-A receptor in the human prostate adenocarcinoma cells (PC-3). The lower graph demonstrates the NPR-C receptor at 66 kiloDaltons (kDa) in the human prostate cancer cells as well as in the positive control (left panel). Beta-galactosidase (130 kDa) and BSA (70 kDa) were used in addition to BIO RAD Precision Plus Protein Dual color standards to identify the bands corresponding to the NPR-A and NPR-C receptors, respectively. Re-probing with Beta-Actin was used as a loading control.

Example II

Small-Cell Lung Cells

This invention is the first evidence that vessel dilator, ANP, LANP, kaliuretic peptide and CNP can decrease the number of human small-cell lung carcinoma cells. All four of the peptide hormones synthesized by the ANP gene, i.e. LANP, vessel dilator, kaliuretic peptide and ANP have been previously investigated by the inventors for their effects on adenocarcinomas, i.e. human pancreatic and breast adenocarcinomas. Similar results were found with human pancreatic and breast adenocarcinomas to each of the four peptide hormones synthesized by the ANP gene decreasing the number of human pancreatic adenocarcinoma cells during the first 24 hours 34% to 65% at their 1-μM concentrations with similar decreases in human breast adenocarcinoma cells. Thus, these four peptide hormones significantly decrease the number of cancer cells in both adenocarcinomas and small-cell lung carcinomas. The present invention indicates therefore that these four peptide hormones significantly decrease the number of cancer cells of at least two different types of cancers within 24 hours. This information, plus the knowledge that one of these peptide hormones, i.e. ANP, decreases the number of hepatoblastoma cells and proliferation in neuroblastoma cells in culture, suggests that these peptide hormones possibly have generalized anticancer effects, i.e. have the ability to decrease the number of cancer cells from a variety of different cancers. The ability of these four peptide hormones to completely stop the growth of human pancreatic adenocarcinomas in vivo with three of the four peptide hormones decreasing the volume of this human cancer up to 50% in 1 week, highlights the clinical cancer treatment relevance of these peptide hormones.

Brain natriuretic peptide and CNP at their 1-μM and 10-μM concentrations did not have similar effect on the number of human small-cell lung cancer cells. Brain natriuretic peptide did not have any significant anticancer effects, even when its concentration was 100-fold higher than the concentration of the four peptide hormones synthesized by the ANP prohormone gene, which significantly decreased the human small-cell cancer cell number. C-natriuretic peptide did have significant effects when its concentration was increased to 100-fold higher than the concentration where the four peptide hormones from the ANP prohormone gene had significant effects (39% decrease).

Figure 7:
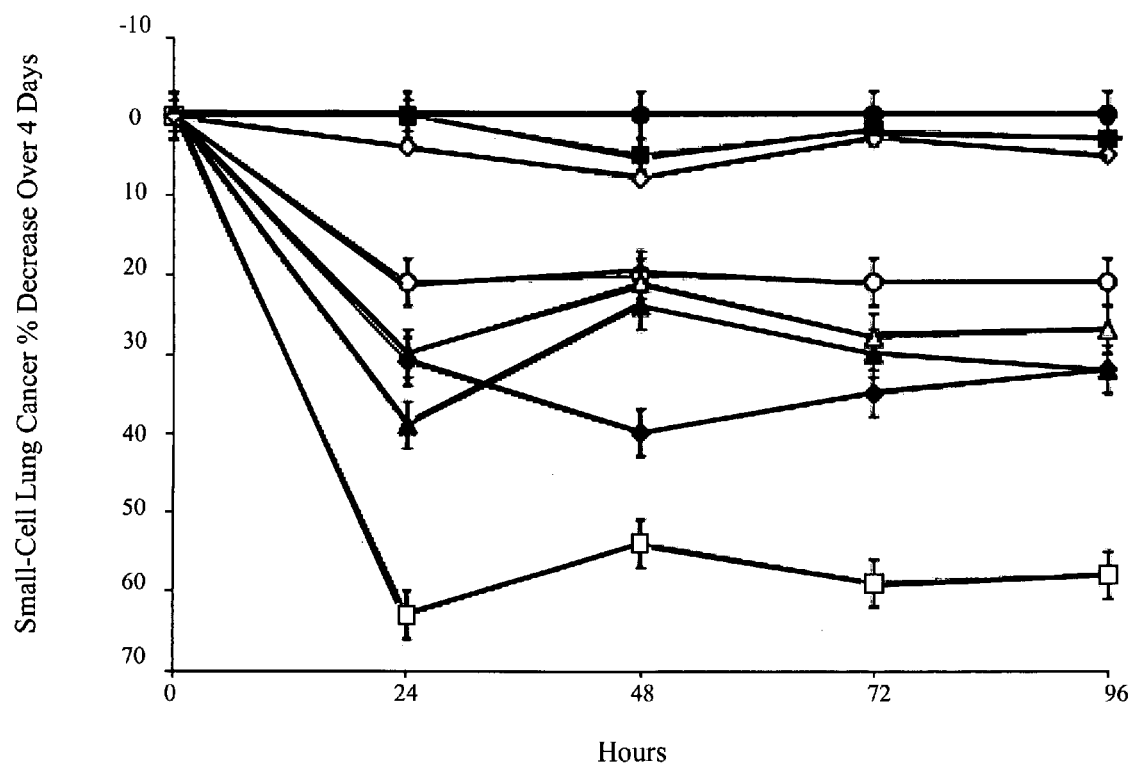
FIG. 7 Time course of decrease in human small-cell lung cancer cell number with 1 µM of the vessel dilator (□), longacting natriuretic peptide (O, LANP), kaliuretic peptide (Δ, atrial natriuretic peptide (ANP, ▲), brain natriuretic peptide (BNP, ■), C-type natriuretic peptide (◇), respectively, and cyclic GMP (cGMP, 1 µM, ♦) compared with placebo-treated (●) small-cell lung cancer cells.

Vessel dilator was the most potent of these peptide hormones in decreasing the number of the small-cell lung cancer cells. Vessel dilator had significant (P<0.001) effects within 24 hours (63% decrease in number of small-cell lung cancer cells) and inhibited any further proliferation of the small-cell lung cancer cells from 24 to 96 hours (P<0.001; FIG. 7). In the dose-response curves of the present investigation, when vessel dilator concentrations were increased 10-fold and 100-fold (i.e. 10 and 100 μM), it decreased the number of human cancer cells 73% and 92% within 24 hours (FIG. 9) with no proliferation of these cancer cells in the 3 days that followed (FIG. 10). After 3 days with 100 μM of vessel dilator, only six human cancer cells (6±0.5 cells) had not been killed. Thus, the vessel nearly eliminated all of the human cancer cells within 24 hours. Vessel dilator also decreased human pancreatic adenocarcinomas in vitro the most and decreased human pancreatic adenocarcinoma tumour volume the most in vivo, demonstrating that it has the most significant anticancer properties of these peptide hormones.

The other three peptide hormones synthesized by the ANP gene effects on decreasing the number of small-cell lung carcinoma cells were significant, however. Atrial natriuretic peptide (1 μM) decreased the number of small-cell carcinoma cells at 24 hours (39% decrease), which is more than its ability to decrease the number of pancreatic adenocarcinoma cells at 24 hours, i.e. 34%. On the other hand, kaliuretic peptide's (1 μM) ability to decrease the number of small-cell lung carcinoma cells at 24 hours was not as good with small-cell lung carcinoma cells (30%) as with human pancreatic adenocarcinoma cells (37%). Thus, there appears to be a difference in these peptide hormones' ability to decrease the cancer cell number depending upon the type of cancer.

When the four peptide hormones that had significant effects at 1 μM were added together (each at 1 μM) for 24 hours they decreased the number of human small-cell lung cancer cells by 62%, which was similar to the ability of the vessel dilator to decrease the number of cancer cells (i.e. 63%) by itself. It should be noted that there was no decrease in the number of cells when examined immediately after addition of the respective peptide hormones, indicating that the data obtained was not owing to artifact. It is also important to note that cellular debris was present after 24 hours of incubation with the four ANP prohormone peptides, suggesting that cellular necrosis was occurring.

Each of the four peptide hormones from the ANP prohormone inhibited 68% to 82% of the amount of DNA synthesis in these small-cell lung carcinoma cells. These findings suggest that one important mechanism of action of these peptide hormones to inhibit cancer cell number and their proliferation is via their ability to inhibit DNA synthesis.

With respect to the mechanism of how these peptide hormones inhibit DNA synthesis, one of the second messengers of their biologic effects, i.e. cyclic GMP, was found using 8-bromo cyclic GMP to inhibit DNA synthesis up to 50% in the small-cell lung carcinoma cells. Cyclic GMP's mimicking of the effects of these peptide hormones on DNA synthesis in the same cells suggests that cyclic GMP is one of the mediators of these peptide hormones' ability to inhibit DNA synthesis in small-cell lung cancer cells. The concentrations of cyclic GMP that inhibited DNA synthesis in the small-cell lung carcinoma cells are identical to the concentrations of cyclic GMP measured within tissues secondary to these peptide hormones. Further evidence that the cyclic GMP inhibition of DNA synthesis in small-cell lung cancer cells may be important for these peptide hormones anticancer growth effects is that whencyclic GMP was infused subcutaneously for a week in athymic mice with human pancreatic adenocarcinomas, it inhibited 95% of the growth of the human pancreatic adenocarcinoma compared with placebo-treated adenocarcinomas.

Both the NPR-A and NPR-C (i.e. clearance) receptors were present in these small-cell lung cancer cells. This knowledge helps to explain BNP's and CNP's lack of biologic effects in these cancer cells at their 1-μM concentrations. Atrial natriuretic peptide binds to both the NPR-A and C-receptors with a higher affinity than BNP or CNP. Binding to the NPR-A receptor is ANP>BNP>>CNP while binding to the NPR-C receptor is ANP>CNP>BNP. Binding of human BNP to the human NPRC receptor is an order of magnitude lower than ANP, indicating that an order of magnitude larger concentration of BNP is necessary to be present for BNP to have effects. In the present investigation the inventors have investigated BNP and CNP, which had no effects at 1 μM whereas the other peptide hormones did, at 10-fold and 100-fold higher concentrations. At 10-fold higher (i.e. 10 μM) concentrations of BNP and CNP, neither significantly decreased the number of human small-cell lung cancer cells. Anticancer effects were observed at the 100-fold higher concentration of CNP, but even at the 100-fold higher concentration no any anticancer properties were found with BNP. The ability of CNP to have effects at 100 μM but not at 100-fold lower concentrations that the other four cardiovascular hormones had effects while BNP still did not have any effect when its concentration was increased 100-fold may relate in part to the ability of these peptide hormones to bind to the NPR-C receptor which may mediate some of these peptides biologic effects as described below. Binding to the NPR-C receptor is ANP>CNP<BNP. Thus, ANP, which binds more avidly to this receptor, had effects at 100-fold lower concentrations than CNP, which is next in affinity for this receptor, while BNP, which has the lowest affinity for this receptor, had no anticancer effects. As the NPR-A receptor is thought to be the active receptor mediating ANP, BNP and CNP effects, part of the anticancer effects found with ANP may be mediated through this receptor found to be present in the small-cell lung cancer cells.

The NPR-C receptor was demonstrated to be present for the first time in the present invention in human small-cell lung cancer cells. Although the NPR-C receptor (i.e. clearance receptor) has been thought to mainly clear ANP, BNP, and CNP from the circulation, as it does not have guanylate cyclase or protein kinase attached to it, as with the NPR-A receptor, to produce cyclic GMP which is the main mediator of ANP, BNP, and CNP effects, there is evidence now that ANP may signal via the NPR-C receptor in smooth muscle cells. In smooth muscle cells, ANP after binding to the NPR-C receptor initiates a signal cascade consisting of a Ca2+ influx, and activation of endothelial nitric oxide synthase with resulting formation of nitric oxide activating cytosolic guanylate cyclase, which in turn increases the concentration of the intracellular mediator cyclic GMP. This would be a mechanism of increasing cyclic GMP without utilizing the NPR-A receptor to help mediate the cyclic GMP effects of decreasing smallcell lung cancer cell number and DNA synthesis found in the present investigation.

Small-Cell Lung Cancer Cells

A cell line (ATCC number CRL-2195, SHP-77) was derived in 1977 by E. R. Fisher, A. Palekar and J. D. Paulson from a nonencapsulated primary lung tumour from the apical portion of the upper lobe of the left lung of a 54-year-old Caucasian man. These cells, when injected into athymic mice, form tumours with a doubling time of 96 hours.

Culture of the Small-Cell Lung Carcinoma Cells

Propagation of these cells was in Roswell Park Memorial Institute (RPMI) 1640 medium with 2 mM $L^{-1}$-glutamine adjusted with addition of 1.5 g $L^{-1}$ sodium bicarbonate, 4.5 g $L^{-1}$ glucose, 10 mM HEPES, 1 mM of 90% sodium pyruvate and heat-inactivated 10% fetal bovine serum at a temperature of 37° C., as recommended by the ATCC. Cells were dispensed into new flasks with subculturing every 6-8 days. The growth medium was changed every 3 days.

Research Protocol

The research protocol for the small-cell lung carcinoma cells was similar to that of the of the prostate adenocarcinoma cells discussed above. The protocol varied in that After subculturing for 24 hours, the small-cell lung carcinoma cells were then seeded to coverslips in 24-well plates with 1 mL of the abovementioned RPMI media (rather than Ham's F12k media as discussed above).

Determination of DNA Synthesis

To investigate whether these peptide hormones were inhibiting DNA synthesis, bromodeoxyuridine (BrdU) incorporation into the small-cell lung carcinoma cells was utilized. Bromodeoxyuridine was from BD Bioscience, San Jose, Calif. DNA synthesis and doubling of the genome take place during the synthetic or S phase. Bromodeoxyuridine is a thymidine analogue incorporated into nuclear DNA during the S phase of the cell cycle. After 24 hours in culture with 1 μM of LANP, vessel dilator, kaliuretic peptide, ANP, BNP, or CNP, respectively, or with no peptide hormone (i.e. control), BrdU in a final concentration of 10 μM in the cell culture medium was added for 45 min: the time in which the cells are in the logarithmic phase of cell proliferation. For immunohistochemistry, a BrdU in situ detection kit was utilized. Incorporation of the BrdU stain into the nucleus was counted using a Nikon Inverted Diaphot-TMD Microscope. The number of stained nuclei were compared in the six peptide hormone groups to the positive control group. BrdU incorporation by immunochemistry has been demonstrated to be equally good as $^3$H-thymidine incorporation, with the advantage of providing high resolution.

ANP Receptors in Small-Cell Lung Carcinoma Cells

On finding that these ANPs decreased the number of human small-cell carcinoma cells, it was then evaluated whether small-cell lung carcinomas have ANP receptors to mediate these effects. Western blots of the natriuretic peptide receptors (NPRs) A- and C- were performed as follows.

Western Blotting

Seventy-five micrograms of protein extract from small-cell lung carcinoma cells, measured using the bicinchonic acid (BCA) protein assay kit, was loaded onto each lane of a Criterion Precast 7.5% Tris-HCl gel, separated by electrophoresis (200 V for 60 min), and then transblotted onto a nitrocellulose membrane Hybond-C Extra, for 75 min at 100 V in Towbin buffer. Blots were blocked for 1 hours at room temperature in a 5% solution of dry milk, washed×3 with Trisbuffered saline, and then incubated for 1 hours in a 5% solution of bovine serum albumin in Tris-buffered saline containing a 1:4000 dilution of A035 polyclonal antibody directed against the COOH terminus of the NPR-A receptor protein or containing Tris-buffered saline with a 1:1000 dilution of antibody to the NPR-C receptor. After being washed×4 with Tris-buffered saline, the membranes were incubated for 1 hours at room temperature in a solution of dry milk with a 1:6000 and 1:3000 dilutions of goat antirabbit IgG antibody for the NPR-A and NPR-C receptors, respectively. After three washings with Tris-buffered saline, the bands were identified by enhanced chemiluminescence reagents and visualized in a luminescent image analyzer. Specificity was revealed by the presence of a signal in rat lung (positive control) and absence of a signal with normal rabbit serum, rabbit IgG, and after preabsorption of the NPR-A antibody with NPR-A protein or preabsorption of the NPRC antibody with NPR-C protein. Monoclonal anti-B-actin antibody (Sigma) was used as a loading control.

Decrease in number of small-cell carcinoma cells by four peptide hormones synthesized by the ANP gene.

Figure 6:
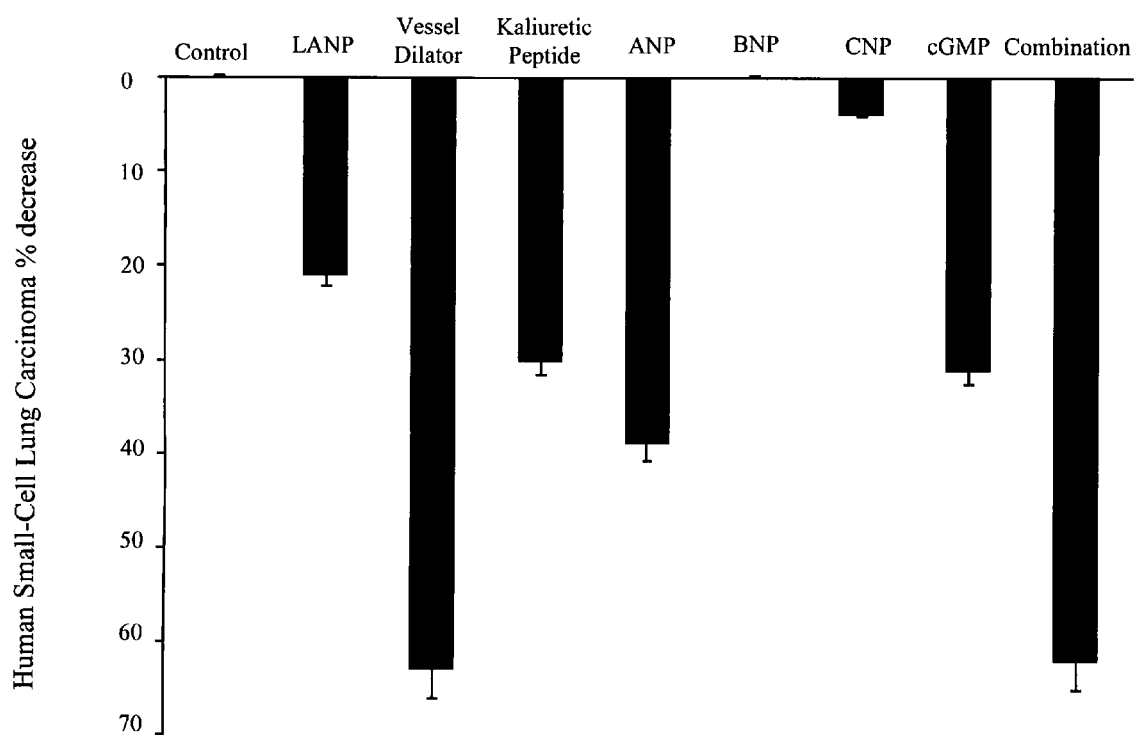
FIG. 6 Is a graph showing the decrease in human small-cell lung cancer cells after a 24-h exposure to 1 µM of long acting natriuretic peptide (LANP), vessel dilator, kaliuretic peptide, atrial natriuretic peptide (ANP), brain natriuretic peptide (BNP) and C-type natriuretic peptide (CNP).

The number of small-cell lung carcinoma cells after 24 hours without the addition of any of the peptide hormones averaged 86±9 cells per high-powered field when 10 fields of the coverslip were evaluated at ×40 along the X-axis. This evaluation was repeated on six separate occasions with the above number reflecting 60 observations of the number of control small-cell lung carcinoma cells and 60 observations of each of the six groups with addition of one of the cardiac hormones (FIG. 6). The addition of 1 μM of LANP for 24 hours decreased the number of human small-cell lung carcinoma cells to 68±6, i.e. a 21% decrease (P<0.05) in the number of small-cell carcinoma cells with the LANP (FIG. 6). Vessel dilator at 1 μM for 24 hours had an even more dramatic decrease (63%; P<0.001) in the number of the human small-cell lung carcinoma cells (FIG. 6). Vessel dilator decreased the number of lung cancer cells from 86±9 cells to 32±4. Kaliuretic peptide at 1 μM for 24 hours decreased the number of human small-cell lung carcinoma cells 30% (P<0.05), i.e. to 60±6 small-cell lung cancer cells (FIG. 6).

The decrease in small-cell lung cancer cells was significant at P<0.001 with the vessel dilator, P<0.01 with ANP, and P<0.05 with kaliuretic peptide and LANP when evaluated by repeated analysis of variance (ANOVA). There was no significant decrease in small-cell lung cancer cell number secondary to BNP or CNP when evaluated by ANOVA. The decrease in number of small-cell lung cancer cells secondary to the vessel dilator was significantly greater (P<0.05) than the decrease secondary to any of the other natriuretic peptides when evaluated by ANOVA. Cyclic GMP's (cGMP) (1 μM) decrease in small-cell lung cancer cells was significant at P<0.05 when evaluated by ANOVA. Combination of the four peptide hormones that had significant effects, i.e. vessel dilator, LANP, kaliuretic and ANP (each at 1 μM), caused a very significant (P<0.001) decrease in the number of human small-cell lung cancer cells, but this decrease was no more significant than that caused by the vessel dilator alone when evaluated by ANOVA.

The number of human small-cell lung cancer cells in culture decreased 39% (P<0.05) when exposed to ANP 1 μM for 24 hours (FIG. 6). Brain natriuretic peptide and CNP, each at 1 μM, only decreased the number of small-cell lung carcinoma cells 0% and 4%, respectively, after 24 hours of incubation (not significant). Thus, with respect to their ability to inhibit the growth of human small-cell carcinoma cells when these cells were exposed to identical concentrations of these six peptide hormones for 24 hours, vessel dilator>ANP>kaliuretic peptide>LANP>CNP>BNP. Adding the four peptide hormones which had significant effects together (each at 1 μM) resulted in a 62% decrease (i.e. similar to vessel dilator alone) in human small-cell cancer cell number (FIG. 6). When the number of cells was examined immediately after the incubation of the respective peptide hormones within the cells, there was no decrease in the number of cancer cells. In the wells with decreased number of cells secondary to the cardiac hormones, there was evidence of cellular debris.

Decreased Cellular Proliferation after Initial Decrease in Small-Cell Lung Carcinoma Cell Number When small-cell lung cancer cells were exposed for longer periods of time, e.g. 48, 72, and 96 hours to the vessel dilator, LANP, kaliuretic peptide, ANP, BNP, and CNP each at 1 μM, there was a inhibition of proliferation of the small-cell lung carcinoma cells after the decrease in the number of these cancer cells at 24 hours by the peptide hormones from the ANP gene (FIG. 7). Thus, when exposed to the vessel dilator, LANP, kaliuretic peptide and ANP for 48 hours, the inhibition of the number of cancer cells compared with untreated small-cell carcinoma cancer cells was 54% (P<0.001), 20%, 21% and 24% (P<0.05 for these three peptides), respectively. At 72 hours and 96 hours, the decrease in number of small-cell carcinoma cells secondary to the vessel dilator was 59% and 58% (P<0.001, FIG. 7). At both 72 and 96 hours, the number of small-cell carcinoma cells was reduced 21% by LANP (P<0.05 for both) compared with untreated small-cell lung cancer cells at these time periods. At 72 and 96 hours, the number of cancer cells with kaliuretic peptide present was decreased by 28% and 27%, respectively, compared with untreated small-cell lung carcinoma cells (P<0.05 for each) (FIG. 7). The number of small-cell lung cancer cells at 72 and 96 hours decreased secondary to ANP 30% and 32% (P<0.05 for both) compared with the number of small-cell lung cancer cells at these same time periods without the addition of any peptide hormone (FIG. 7). Thus, proliferation was inhibited by these cardiac peptide hormones for 3 days after the initial decrease in cell number in the first 24 hours (FIG. 7). There was no significant increase in proliferation of any of the cancer cells when exposed to these four peptide hormones for 1, 2, and 3 days after the initial decrease in number of the small-cell lung cancer cells within the first 24 hours. There was no significant decrease in small-cell lung cancer number secondary to BNP or CNP (each at 1 µM) at 48, 72, or 96 hours (FIG. 7).

The decrease in cancer cell number by ANP, LANP, kaliuretic peptide, and cGMP were significant at P<0.05 while the decrease secondary to the vessel dilator was significant at P<0.001 at each time-point compared with placebo when evaluated by repeated analysis of variance (ANOVA). There was no significant decrease in small-cell lung cancer cell number with either BNP or CNP when evaluated by repeated ANOVA.

Dose-Response Studies

Figure 8:
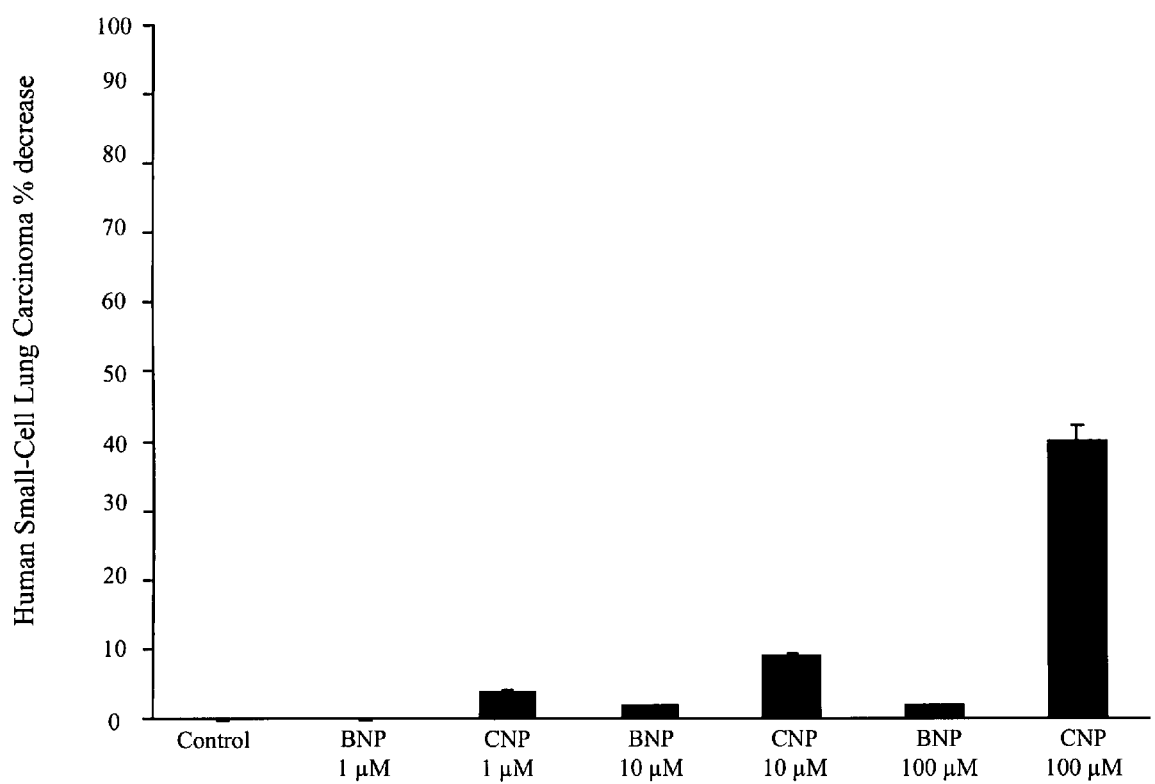
FIG. 8 Evaluation of brain natriuretic peptide (BNP) and C-type natriuretic peptide (CNP) at 10-fold and 100-fold higher concentrations than the concentration (1 µM) that caused a significant decrease in human small-cell lung cancer cell number with the other four cardiovascular hormones.

As BNP and CNP had no effects at 1 µM, the next question asked was whether they might have effects at 10- and 100-fold higher concentrations. When evaluated at 10-fold higher concentrations (i.e. 10 µM) BNP and CNP decreased the number of human small-cell lung cancer cells 2% and 9%, respectively (nonsignificant) (FIG. 8). Increasing BNP and CNP concentrations 100-fold to 100 µM resulted in BNP decreasing the number of cancer cells 1% (not significant), but CNP at this concentration decreased the number of cells by 39% (P<0.05; FIG. 8). When CNP's effects were evaluated over time at these higher concentrations, CNP at 10 µM decreased the number of cancer cells at 24, 48, 72, and 96 hours 9%, 9%, 9% and 9%, respectively (nonsignificant). At 100 µM, CNP, during this same time period, decreased the number of small-cell lung cancer cells 39%, 39%, 39%, and 38%, respectively (P<0.05).

Neither BNP or CNP had any significant effects on the small-cell lung cancer cell number at their 10-fold higher concentrations (i.e. 10 µM). At a 100-fold higher concentration (i.e. 100 µM), BNP still had no effect on the small-cell lung cancer cell number, but CNP did cause a decrease in cell number which was significant (P<0.05) when evaluated by ANOVA.

Figure 9:
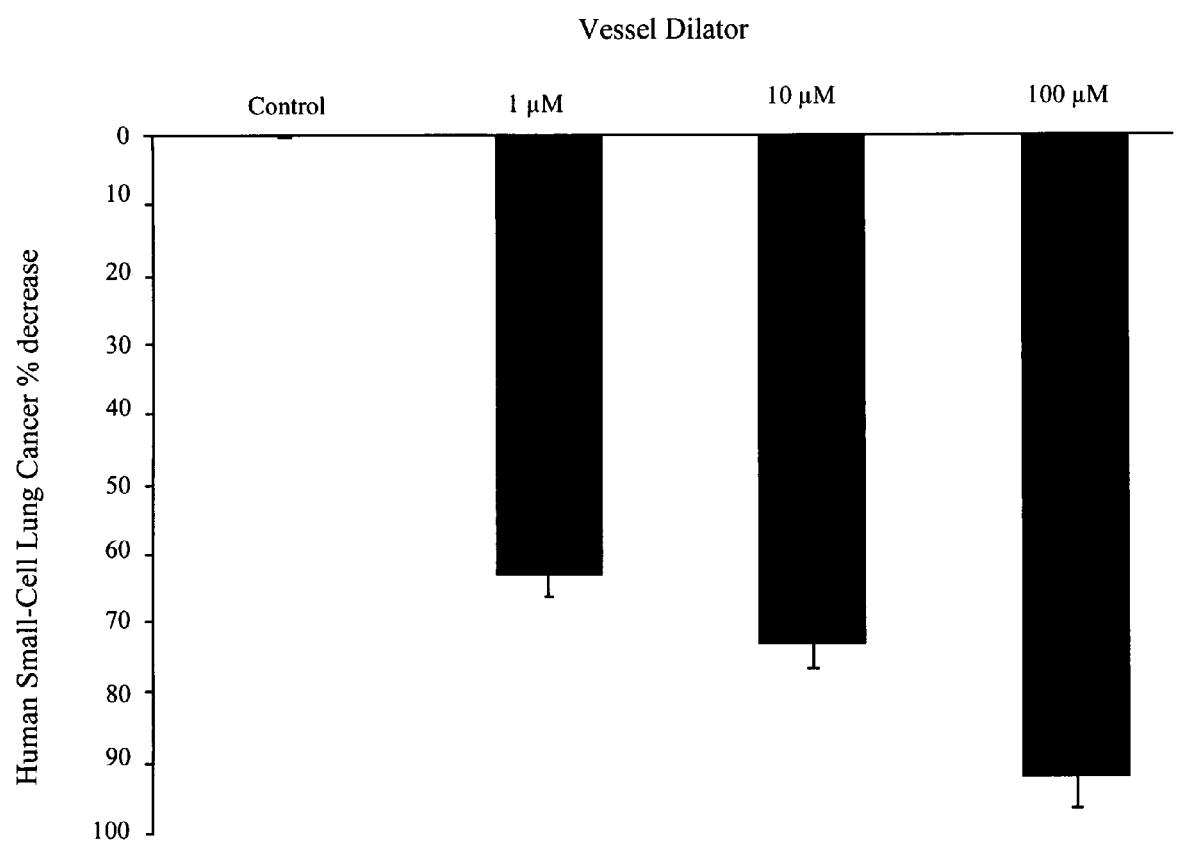
FIG. 9 Dose-response curves of the vessel dilator on the number of human small-cell lung cancer cells.
Figure 10:
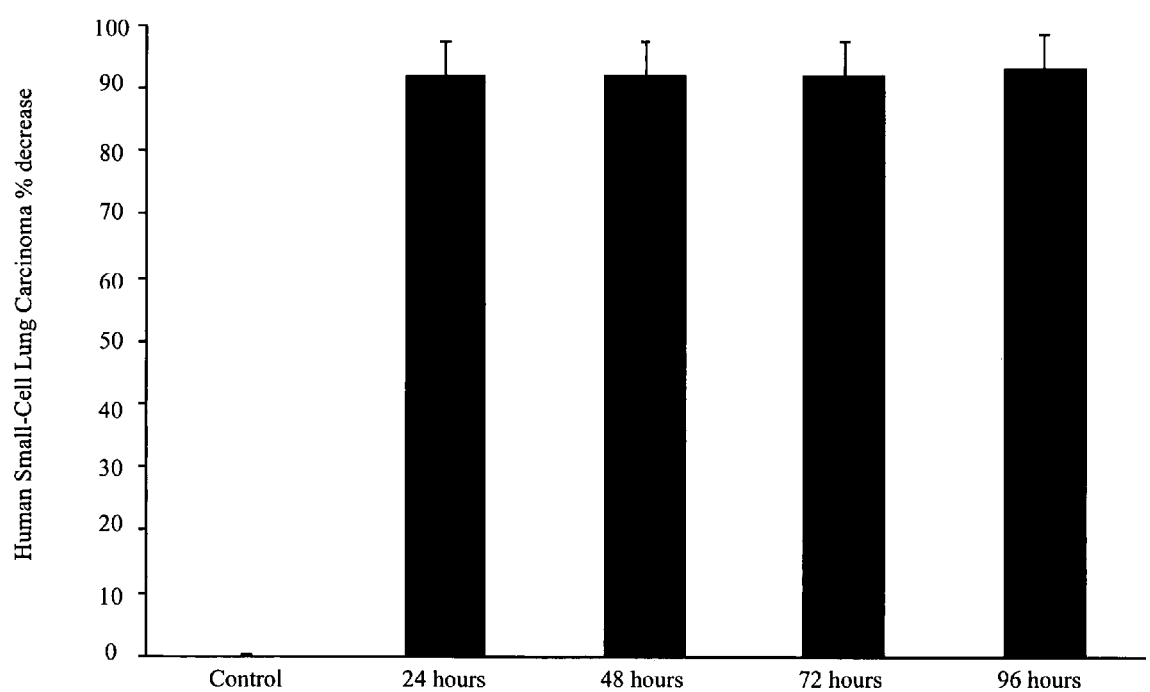
FIG. 10 Sustained 92% or greater decrease in human small-cell lung cancer cell number compared with the untreated (control) cancer cells over 4 days secondary to the 100-µM concentration of the vessel dilator.

Similar dose-response curves revealed that the vessel dilator that decreased the number of human small-cell lung cancer cells 63% at 1 µM further decreased the number of cancer 73% at 10 µM and 92% at 100 µM (FIG. 9).

At concentrations of 1 µM and higher, the decrease in human small-cell lung cancer cells was significant at P<0.001 when evaluated by ANOVA. Comparison of the effects of the different concentrations of the vessel dilator revealed that a significantly (P<0.05) greater decrease (92% in cancer cell number) was observed at the 100-µM concentration compared with the 1-µM concentration (63% decrease in cancer cell number within 24 hours) secondary to the vessel dilator when evaluated by a paired t-test.

At a 10-µM concentration of the vessel dilator the decrease in human cancer cells at 48, 72, and 96 hours was identical to the decrease at 24 hours. When the vessel dilator's effects were examined at 100 µM at 24, 48, 72, and 96 hours the decrease in the number of cancer cells was 92%, 92%, 92%, and 93% (P<0.001), respectively (FIG. 10).

The respective decreases in the human small-cell lung cancer cell number at each time point were significant at P<0.001 compared with untreated human cancer cells when evaluated by ANOVA. Thus, the vessel dilator at 100 µM eliminated almost all the human small-cell lung cancer cells within 24 hours (i.e. there were only 6±0.5 cells left), and these effects were sustained with no proliferation of the cancer cells in the 3 days after this very significant (P<0.001) decrease in the number of human cancer cells.

Cyclic GMP Decreases Small-Cell Lung Cancer Cell Number

Cyclic GMP at 1 µM decreased the number of human small-cell lung cancer cells by 31% at 24 hours (FIG. 6). The decrease in the number of human small-cell carcinoma cells at 48, 72, and 96 hours was 40%, 35%, and 32%, respectively (P<0.05 at all time points compared with control) (FIG. 7).

Inhibition of DNA Synthesis by Four Peptide Hormones

To help determine the mechanism of the small-cell lung carcinoma cells' decrease in number and decreased cellular proliferation by the above four peptide hormones, the inventors next investigated whether their effects were owing to an inhibition of DNA synthesis, as they have been demonstrated to decrease DNA synthesis in pancreatic and breast adenocarcinoma cells. Vessel dilator, LANP, kaliuretic peptide and ANP each at their 1-µM concentrations inhibited DNA synthesis when incubated with human small-cell lung carcinoma cells for 24 hours by 82%, 75%, 68% and 78%, respectively (P<0.001 for each) (FIG. 8). There was no significant decrease in DNA synthesis at 1 µM in the small-cell lung cancer cells secondary to BNP or CNP (FIG. 8).

Cyclic GMP Inhibits DNA Synthesis in Small-Cell Lung Cancer Cells

Figure 11:
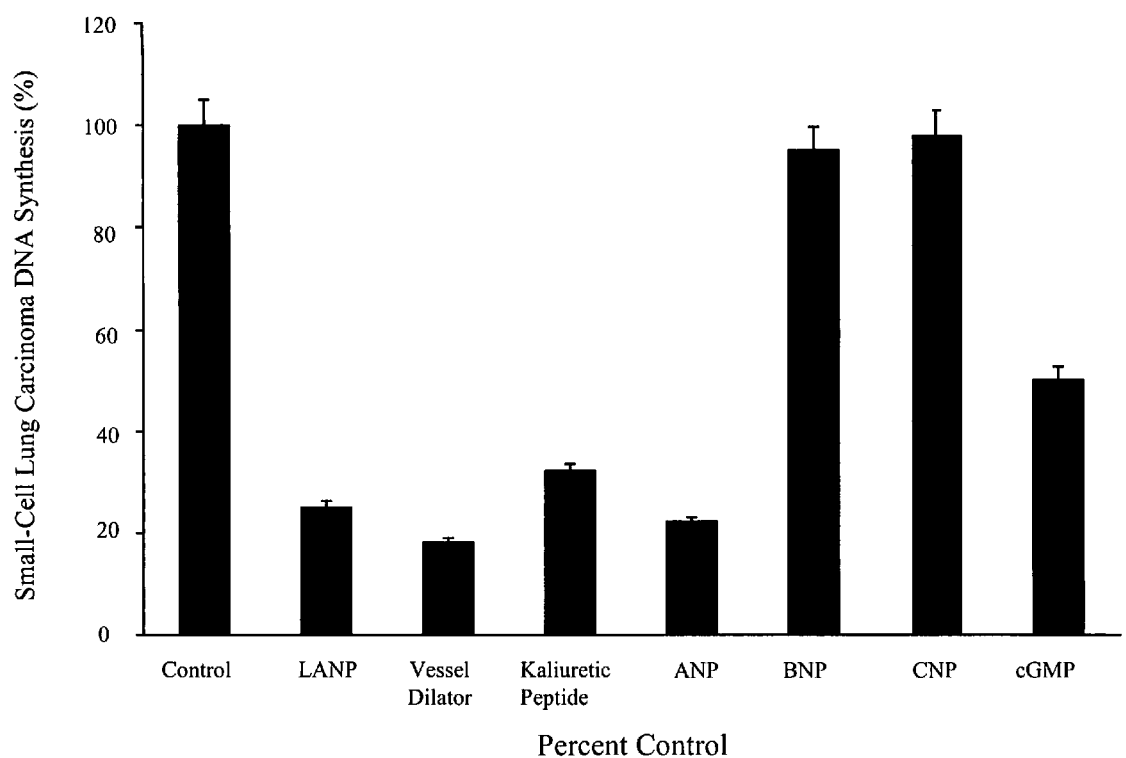
FIG. 11 is a graph demonstrating inhibition of DNA synthesis by the vessel dilator, long-acting natriuretic peptide (LANP), kaliuretic peptide, and atrial natriuretic peptide (ANP) in human small-cell lung cancer cells.

To help define the mechanism(s) for these peptide hormone's ability to decrease DNA synthesis, one of the known mediators of these peptides biologic effects, i.e. cyclic GMP, was investigated to determine whether it could inhibit DNA synthesis in these same small-cell lung cancer cells. 8-bromo cyclic GMP decreased DNA synthesis in small-cell lung carcinoma cells by 50% (P<0.01) at its 1-µM concentration (FIG. 11).

This inhibition of DNA synthesis is illustrated as the percent of DNA synthesis occurring with the respective peptide hormones, each at 1 µM, vs. the amount of DNA synthesis without the addition of any of these peptide hormones. The amount of inhibition of DNA synthesis by each of these peptide hormones was significant at P<0.001 when evaluated by repeated analysis of variance (ANOVA). 8-bromo cyclic GMP at its 1-µM concentration inhibited DNA synthesis by 54% in the small-cell lung cancer cells (P<0.01). BNP and CNP, each at 1 µM, had no significant effect on DNA synthesis when evaluated by repeated ANOVA.

NPR-A and -C Receptors are Present in Small-Cell Lung Cancer Cells

Small-cell lung cancer cell lines have been reported to have NPR-A receptors [35] but natriuretic receptors have never been evaluated in the small-cell lung cancer line utilized in the present investigation. It has never previously been investigated whether small-cell lung carcinomas have NPR-C receptors. When the small-cell lung carcinoma cells were evaluated by Western blots, the NPRA- and C-receptors were demonstrated to be present (FIG. 12).

Figure 12:
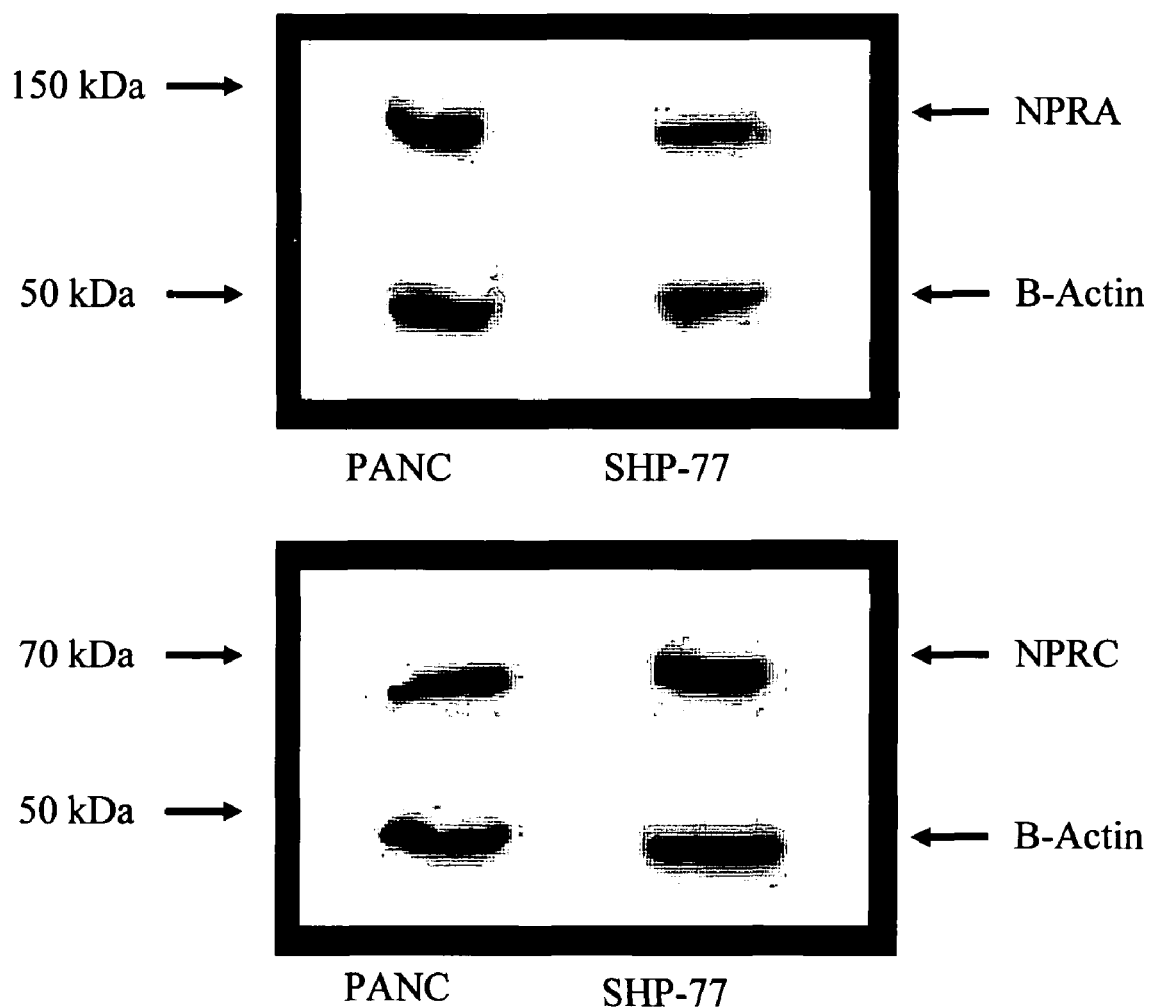
FIG. 12 Western blot of natriuretic peptide receptors (NPRs) A- and C- are present in human small-cell lung cancer cells.

Western blot analysis, FIG. 12, with 1:4000 dilution of A035 polyclonal antibody directed against the COOH terminus of the natriuretic peptide A-receptor (NPRA) and 1:1000 dilution of antibody to the NPR-C receptor. The upper graph demonstrates the positive rat lung control (PANC) for the NPR-A receptor and the NPR-A receptor in the small-cell lung cancer (SHP-77). The lower graph demonstrates the NPR-C receptor at 66-kiloDaltons (kDa) in the human small-cell lung cancer cells (SHP-77) as well as in the positive control (left panel). Beta-galactosidase (130 kDa) and BSA (70 kDa) were used in addition to BIO RAD Precision Plus Protein Dual Colour standards to identify the bands corresponding to the NPR-A and NPR-C receptors, respectively. Re-probing with Beta-Actin was used as a loading control.

Vessel dilator, LANP, kaliuretic peptide and ANP (at 1 μM) and CNP (at 100 μM) significantly decrease the number of human small-cell lung cancer cells within 24 hours and inhibit their proliferation for at least 96 hours. Their mechanism of doing so involves inhibition of DNA synthesis mediated in part by cyclic GMP.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, Remington's Pharmaceutical Sciences (Martin E W [1995] Easton Pa., Mack Publishing Company, 19$^{th}$ ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question. The pharmaceutical composition can be adapted for various forms of administration, including but not limited to oral, subcutaneous, or intravenous administration. Administration can be continuous or at distinct intervals as can be determined by a person skilled in the art.

The administration of the ANP prohormone compounds are administered and dosed in accordance with good medical practice, taking into account the clinical condition of the individual patient, the site and method of administration, scheduling of administration, patient age, sex, body weight, and other factors known to medical practitioners.

A therapeutically effective amount of each respective peptide hormone, or any combination thereof, is that amount necessary to provide a therapeutically effective amount of the corresponding procyanidin in vivo. The amount of prohormone must be effective to achieve a response. In accordance with the present invention, a suitable dose size is a dose that is capable of preventing or alleviating (reducing or eliminating) a symptom in a patient when administered one or more times over a suitable time period. One of skill in the art can readily determine appropriate single dose sizes for systemic administration based on the size of a subject and the route of administration.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of inhibiting the growth of at least one target cancer cell, comprising contacting an effective amount of C-natriuretic peptide (CNP) to at least one target cancer cell.

2. The method of claim 1, wherein the at least one target cancer cell is of a cancer type chosen from the group consisting of an adenocarcinoma, small cell carcinoma, and squamous cell carcinoma.

3. The method of claim 1, wherein the effective amount of CNP is administered to at least one target cancer cell in vivo.

4. The method of claim 3, wherein the mode of administration of the CNP is chosen from the group consisting of oral, subcutaneous, and intravenous administration.

5. The method of claim 3, wherein said administering comprises co-administering an effective amount of a combination of CNP and a peptide hormone derived from the atrial natriuretic peptide (ANP) pro-hormone.

6. The method of claim 5, wherein the peptide hormone derived from the ANP pro-hormone is selected from the group consisting of long acting natriuretic peptide (LANP), vessel dilator, kaliuretic peptide, and ANP.

* * * * *

UNITED STATES PATENT AND TRADEMARK OFFICE
CERTIFICATE OF CORRECTION

| | |
|---|---|
| PATENT NO. | : 7,846,900 B2 |
| APPLICATION NO. | : 12/346192 |
| DATED | : December 7, 2010 |
| INVENTOR(S) | : David L. Vesely |

It is certified that error appears in the above-identified patent and that said Letters Patent is hereby corrected as shown below:

Column 3,
Line 50, "longacting" should read --long acting--.
Line 51, "($\Delta$," should read --($\Delta$),--.

Column 4,
Line 32, "unfortunately is not" should read --unfortunately it is not--.
Line 38, "anti-androgens there is" should read --anti-androgens, there is--.

Column 5,
Lines 15-16, "Thus, vessel nearly" should read --Thus, vessel dilator nearly--.

Column 9,
Line 6, "were specific the inventors" should read --were specific, the inventors--.

Column 10,
Lines 33-34, "decrease (P<0.05) the number" should read
    --decrease (P<0.05) in the number--.

Column 13,
Line 8, "the vessel nearly" should read --the vessel dilator nearly--.
Line 11, "tumour" should read --tumor--.
Lines 14-16, "The other three peptide hormones synthesized by the ANP gene effects on
    decreasing the number of small-cell lung carcinoma cells were significant,
    however." should read
    --The effects of the other three peptide hormones synthesized by the ANP on the
    number of small-cell lung carcinoma cells were significant, however.--.
Lines 59-60, "hormones anticancer growth effects" should read
    --hormones' anticancer growth effects--.
Line 60, "whencyclic" should read --when cyclic--.

Signed and Sealed this
Twenty-ninth Day of March, 2011

David J. Kappos
*Director of the United States Patent and Trademark Office*

CERTIFICATE OF CORRECTION (continued)
U.S. Pat. No. 7,846,900 B2

Column 14,
Line 4, "ANP > BNP >> CNP" should read --ANP > BNP > CNP--.
Line 6, "NPRC receptor" should read --NPR-C receptor--.
Lines 16-17, "concentration no any anticancer" should read
    --concentration, no anticancer--.
Line 25, "ANP > CNP < BNP." should read --ANP > CNP > BNP.--.
Lines 43-44, "ANP after binding to the NPR-C receptor initiates" should read
    --ANP, after binding to the NPR-C receptor, initiates--.
Line 51, "smallcell" should read --small-cell--.

Column 15,
Line 5, "that of the of the prostate" should read --that of the prostate--.
Line 6, "in that After" should read --in that after--.
Line 31, "equally good as" should read --equally as good as--.
Line 43, "was loaded" should read --were loaded--.
Line 47, "for 1 hours" should read --for 1 hour--.
Line 49, "Trisbuffered saline" should read --Tris-buffered saline--.
Lines 55-56, "for 1 hours" should read --for 1 hour--.
Line 65, "NPRC antibody" should read --NPR-C antibody--.

Column 16,
Line 64, "a inhibition" should read --an inhibition--.

Column 17,
Lines 63-64, "number of cancer 73%" should read --number of cancer cells 73%--.

Column 19,
Line 9, "natriuretic peptide A-receptor (NPRA)" should read
    --natriuretic peptide A-receptor (NPR-A)--.